US010683554B2

(12) United States Patent
Kennedy et al.

(10) Patent No.: US 10,683,554 B2
(45) Date of Patent: Jun. 16, 2020

(54) METHODS AND MATERIALS FOR DETECTING SNPS AND ADMINISTERING MEASLES VIRUS VACCINATIONS

(71) Applicant: Mayo Foundation for Medical Education and Research, Rochester, MN (US)

(72) Inventors: Richard B. Kennedy, Rochester, MN (US); Gregory A. Poland, Marco Island, FL (US); Inna G. Ovsyannikova, Rochester, MN (US); Iana H. Haralambieva, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 6 days.

(21) Appl. No.: 15/907,056

(22) Filed: Feb. 27, 2018

(65) Prior Publication Data

US 2018/0305767 A1 Oct. 25, 2018

Related U.S. Application Data

(60) Provisional application No. 62/464,581, filed on Feb. 28, 2017.

(51) Int. Cl.

| | |
|---|---|
| ***A61P 31/12*** | (2006.01) |
| ***A61P 31/14*** | (2006.01) |
| ***A61K 39/12*** | (2006.01) |
| ***A61K 39/165*** | (2006.01) |
| ***A61K 39/39*** | (2006.01) |
| ***C12Q 1/68*** | (2018.01) |
| ***C12Q 1/6886*** | (2018.01) |
| ***A61P 35/00*** | (2006.01) |
| *A61K 39/00* | (2006.01) |

(52) U.S. Cl.

CPC ............ *C12Q 1/6886* (2013.01); *A61K 39/12* (2013.01); *A61K 39/165* (2013.01); *A61K 39/39* (2013.01); *A61P 31/12* (2018.01); *A61P 31/14* (2018.01); *A61P 35/00* (2018.01); *C12Q 1/68* (2013.01); *A61K 2039/55588* (2013.01); *A61K 2039/572* (2013.01); *A61K 2039/575* (2013.01); *C12N 2760/18434* (2013.01); *C12Q 2600/106* (2013.01); *C12Q 2600/156* (2013.01)

(58) Field of Classification Search

None

See application file for complete search history.

(56) References Cited

U.S. PATENT DOCUMENTS

2011/0105343 A1 5/2011 Puledran et al.
2018/0305767 A1 10/2018 Kennedy et al.

OTHER PUBLICATIONS

Poland et al., PLoS Pathogens, Dec. 2011, 7(12): e1002344. (Year: 2011).*

Aletti et al., "Current management strategies for ovarian cancer," Mayo Clin. Proc., 82(6):751-70 (Jun. 2007).

Anders et al., "Detecting differential usage of exons from RNA-seq data," Genome Res., 22:2008-17 (Oct. 2012).

Anders et al., "HTSeq—a Python framework to work with high-throughput sequencing data," Bioinformatics, 31:166-9 (Jan. 2015).

Aref et al., "Measles to the Rescue: A Review of Oncolytic Measles Virus," Viruses, 8(10) pii:E294 (2016).

Atilgan et al., "Anisotropy of fluctuation dynamics of proteins with an elastic network model," Biophys J., 80:505-15 (Jan. 2001).

Bednarczyk et al., "Estimating the Number of Measles-Susceptible Children and Adolescents in the United States Using Data From the National Immunization Survey-Teen (NIS-Teen)," American Journal of Epidemiology, 184:148-56 (Jul. 2016) doi: 10.1093/aje/kwv320.

Benjamini et al. "Controlling the false discovery rate: a practical and powerful approach to multiple testing," Journal of the Royal Statistical Society Series B, 57:289-300 (Jan. 1995).

Blechacz et al., "Engineered measles virus as a novel oncolytic viral therapy system for hepatocellular carcinoma," Hepatology. 44(6):1465-77 (Dec. 2006).

Brandler et al., "Pediatric measles vaccine expressing a dengue tetravalent antigen elicits neutralizing antibodies against all four dengue viruses," Vaccine, 28(41):6730 (Sep. 2010).

Buchholz et al., "Cell entry by measles virus: Long hybrid receptors uncouple binding from membrane fusion," Virology 70: 3716-3723 (Jun. 1996).

Buchholz et al., "Selective Expression of a Subset of Measles Virus Receptor-Competent CD46 Isoforms in Human Brain," Virology, Mar. 1996, 217(1): 349-355.

Cattaneo, "Four viruses, two bacteria, and one receptor: membrane cofactor protein (CD46) as pathogens' magnet," J Virol. 78:4385-4388 (May 2004).

Chen et al., "The structure of the fusion glycoprotein of Newcastle disease virus suggests a novel paradigm for the molecular mechanism of membrane fusion," Structure, 9:255-66 (Mar. 2001).

Chennubhotla et al., "Signal propagation in proteins and relation to equilibrium fluctuations," PLoS Comput. Biol., 3:1716-26 (Sep. 2007).

Clifford et al., "CD46 measles virus receptor polymorphisms influence receptor protein expression and primary measles vaccine responses in naive Australian children," Clin.Vaccine Immunol. 19:704-710 (May 2012).

Coulombe-Huntington "Fine-scale variation and genetic determinants of alternative splicing across individuals,". PLoS genetics 5:e1000766 (Dec. 2006) doi: 10.1371/journal.pgen.1000766.

Cox et al. "Parameter orthogonality and approximate conditional inference," J. Royal Stat. Soc. Ser. B Methodol., 49:1-39 (Jan. 1987).

(Continued)

*Primary Examiner* — Nicole Kinsey White

(74) *Attorney, Agent, or Firm* — Fish & Richardson P.C.

(57) ABSTRACT

This document provides methods and materials involved in using measles viruses. For example, methods and materials for identifying mammals (e.g., humans) likely to respond to standard measles virus vaccines or standard measles virus-based therapies as well as methods and materials for identifying mammals (e.g., humans) unlikely to respond to standard measles virus vaccines or standard measles virus-based therapies are provided.

6 Claims, 17 Drawing Sheets

Specification includes a Sequence Listing.

(56) References Cited

OTHER PUBLICATIONS

Delaneau et al., "Improved whole-chromosome phasing for disease and population genetic studies," Nat. Methods, 10:5-6 (Jan. 2013).
Dhiman et al., "Variations in measles vaccine-specific humoral immunity by polymorphisms in SLAM and CD46 measles virus receptors," J Allergy Clin Immunol, Sep. 2007, 120(3): 666-672 (Sep. 2007).
Dispenzieri et al., "Smoldering multiple myeloma requiring treatment: time for a new definition?," Blood, 122(26):4172-81 (Dec. 2013).
Elsedawy et al., "Oncolytic vaccines," Expert Rev. Vaccines., 12(10):115 (Oct. 2013).
Feenstra et al., "Common variants associated with general and MMR vaccine-related febrile seizures," Nat Genet, 2014, 46: 1274-1282 (Dec. 2014).
Fraser et al., "Common polymorphic transcript variation in human disease," Genome research 19:567-75 (Apr. 2009) doi: 10.1101/gr.083477.108.
Fuchs et al., "CD46-induced human Treg enhance B-cell responses," European Journal of Immunology, 39:3097-109 (Nov. 2009) doi: 10.1002/eji.200939392.
Grunewald et al., "Targeted Therapies for Ovarian Cancer," Best Pract. Res. Clin. Obstet. Gynaecol., pii: S1521-6934(16)30142-0 (Dec. 2016).
Harahap-Carrillo et al., "Immunogenic Subviral Particles Displaying Domain III of Dengue 2 Envelope Protein Vectored by Measles Virus," Vaccines (Basel), 3(3):50 (Jul. 2015).
Haralambieva et al., "A large observational study to concurrently assess persistence of measles specific B-cell and T-cell immunity in individuals following two doses of MMR vaccine," Vaccine, 29:4485-4491 (Jun. 2011).
Haralambieva et al., "Associations between single nucleotide polymorphisms and haplotypes in cytokine and cytokine receptor genes and immunity to measles vaccination," Vaccine, 29:7883-7895 (Oct. 2011).
Haralambieva et al., "Genetic polymorphisms in host antiviral genes: associations with humoral and cellular immunity to measles vaccine," Vaccine, 29:8988-8997 (Nov. 2011).
Haralambieva et al., "Genome-wide characterization of transcriptional patterns in high and low antibody responders to rubella vaccination," PLos One, 8(5):e62149 (May 2013).
Haralambieva et al., "The genetic basis for interindividual immune response variation to measles vaccine: new understanding and new vaccine approaches," Expert Review of Vaccines 12:57-70 (Jan. 2013) doi: 10.1586/erv.12.134.
Haralambieva et al., "Variability in Humoral Immunity to Measles Vaccine: New Developments," Trends in Molecular Medicine, 21: 789-801 (Dec. 2015) doi: 10.1016/j.molmed.2015.10.005.
Haralambieva et al., "Whole Transcriptome Profiling Identifies CD93 and Other Plasma Cell Survival Factor Genes Associated with Measles-Specific Antibody Response after Vaccination," PLos One, 11:e0160970 (Aug. 2016).
Howie et al., "A flexible and accurate genotype imputation method for the next generation of genome-wide association studies," PLoS Genet., 5:e1000529 (Jun. 2009).
Hull et al., "Identification of Common Genetic Variation That Modulates Alternative Splicing," PLoS Genet, Jun. 2007, 3(6): e99.
Iwata et al., "Modulation of complement regulatory function and measles virus receptor function by the serine-threonine-rich domains of membrane cofactor protein (CD46)," The Biochemical Journal, 304 (Pt 1):169-75 (Nov. 1994).
Johnson et al., "Medical management of high-grade astrocytoma: current and emerging therapies," Semin. Oncol., 41(4):511-22 (Aug. 2014).
Kennedy et al., "Genome-wide analysis of polymorphisms associated with cytokine responses in smallpox vaccine recipients," Human Genetics, 131:1403-1421 (Sep. 2012).
Kennedy et al., "Genome-wide genetic associations with IFNγ response to smallpox vaccine," Human Genetics, 131:1433-1451 (Sep. 2012).
Kennedy et al., "Multigenic control of measles vaccine immunity mediated by polymorphisms in measles receptor, innate pathway, and cytokine genes," Vaccine, 30:2159-2167 (Mar. 2012).
Kennedy et al., "Transcriptomic profiles of high and low antibody responders to smallpox vaccine," Genes and Immunity, 14:277-285 (Jul.-Aug. 2013).
Lambert et al., "Polymorphisms in HLA-DPB1 are associated with differences in rubella virus-specific humoral immunity after vaccination," J. Infect. Dis., 211:898-905 (Mar. 2015).
Langmead et al., "Ultrafast and memory-efficient alignment of short DNA sequences to the human genome," Genome Biol.,10:R25 (Mar. 2009).
Lappalainen et al., "Transcriptome and genome sequencing uncovers functional variation in humans," Nature, 501:506-11 (Sep. 2013) doi: 10.1038/nature12531.
Lech et al., "Use of attenuated paramyxoviruses for cancer therapy," Expert Rev. Vaccines, 9(11):1275 (Nov. 2010).
Lin et al., "The Host Cell Receptors for Measles Virus and Their Interaction with the Viral Hemagglutinin (H) Protein," Viruses, 8(9) pii:E250 (2016).
Liszewski et al., "Membrane cofactor protein (CD46) of complement. Processing differences related to alternatively spliced cytoplasmic domains," The Journal of Biological Chemistry, 269:10776-9 (Apr. 1994).
Manchester et al., "Multiple isoforms of CD46 (membrane cofactor protein) serve as receptors for measles virus," Proceedings of the National Academy of Sciences of the United States of America 91:2161-2165 (Mar. 1994).
Manolio, "Genomewide association studies and assessment of the risk of disease," The New England Journal of Medicine, 363:166-76 (Jul. 2010).
Marie et al., "Linking innate and acquired immunity: divergent role of CD46 cytoplasmic domains in T cell induced inflammation," Nature immunology, 3:659-66 (Jul. 2002).
McCarthy et al., "Differential expression analysis of multifactor RNA-Seq experiments with respect to biological variation," Nucleic Acids Research, 40:4288-97 (May 2012).
McCarthy et al., "Genome-wide association studies for complex traits: consensus, uncertainty and challenges," Nat. Rev Genet. 9:356-369 (May 2008).
Mikhael et al., "Corrections," Mayo Clin. Proc., 88(7):777 (Jul. 2013).
Msaouel et al., "Attenuated oncolytic measles virus strains as cancer therapeutics," Curr. Pharm. Biotechnol., 13(9):1732 (Jul. 2012).
Msaouel et al., "Oncolytic measles virus strains as novel anticancer agents," Expert Opin. Biol. Ther., 13(4):483 (Apr. 2013).
Navaratnarajah et al., "The heads of the measles virus attachment protein move to transmit the fusion-triggering signal," Nat. Struct. Mol. Biol., 18:128-134 (Feb. 2011).
Novembre et al., "Genes mirror geography within Europe," Nature, 456:98-101 (Nov. 2008).
Ovsyannikova et al., "Associations between polymorphisms in the antiviral TRIM genes and measles vaccine immunity," Human Immunology, 74:768-74 (Jun. 2013).
Ovsyannikova et al., "Consistency of HLA associations between two independent measles vaccine cohorts: a replication study," Vaccine, 30:2146-2152 (Mar. 2012).
Ovsyannikova et al., "Effects of vitamin A and D receptor gene polymorphisms/haplotypes on immune responses to measles vaccine," Pharmacogenet. Genomics, 22:20-31 (Jan. 2012).
Ovsyannikova et al., "Genome-wide association study of antibody response to smallpox vaccine," Vaccine, 30:4182-4189 (Jun. 2012).
Ovsyannikova et al., "HLA alleles associated with the adaptive immune response to smallpox vaccine: a replication study," Human Genetics, 133:1083-92 (Sep. 2014).
Ovsyannikova et al., "Single-nucleotide polymorphism associations in common with immune responses to measles and rubella vaccines," Immunogenetics, 66(11):663-669 (Nov. 2014).
Ovsyannikova et al., "The association of CD46, SLAM and CD209 cellular receptor gene SNPs with variations in measles vaccine-

(56) References Cited

OTHER PUBLICATIONS induced immune responses: a replication study and examination of novel polymorphisms," Hum Hered, 72(3): 206-223 (Nov. 2011).
Ovsyannikova et al., "The role of polymorphisms in Toll-like receptors and their associated intracellular signaling genes in measles vaccine immunity," Human Genetics, 130:547-561 (Oct. 2011).
Pe'er et al., "Estimation of the multiple testing burden for genomewide association studies of nearly all common variants," Genetic Epidemiology, 32:381-5 (May 2008).
Persson et al., "Structure of the extracellular portion of CD46 provides insights into its interactions with complement proteins and pathogens," PLoS Pathogens, 6:e1001122 (Sep. 2010).
Pieper et al., "MODBASE, a database of annotated comparative protein structure models, and associated resources.," Nucl. Acids Res., 32:D217-22 (Jan. 2004).
Poland et al., "The re-emergence of measles in developed countries: time to develop the next-generation measles vaccines?," Vaccine, 30:103-104 (Jan. 2012).
Post et al., "Membrane cofactor protein of the complement system: alternative splicing of serine/threonine/proline-rich exons and cytoplasmic tails produces multiple isoforms that correlate with protein phenotype," J Exp Med., 174: 93-102 (Jul. 1991).
Prevention CfDCa (2015) Measles Cases and Outbreaks. http://www.cdc.gov/measles/cases-outbreaks.html. http://www.cdc.gov/measles/cases-outbreaks.html. Accessed Feb. 12, 2015 2015.
Price et al., "Principal components analysis corrects for stratification in genome-wide association studies," Nature Genetics, 38:904-909 (Aug. 2006).
Prince et al., "Principal components analysis corrects for stratification in genome-wide association studies," Nature Genetics, 38:904-909 (Aug. 2006).
Pritchard et al., "Inference of population structure using multilocus genotype data," Genetics, 155:945-959 (2000).
Purcell et al., "PLINK: a tool set for whole-genome association and population-based linkage analyses," Am. J. Hum. Genet., 81:559-575 (Sep. 2007).
Quinlan et al., "BEDTools: a flexible suite of utilities for comparing genomic features," Bioinformatics, 26:841-2 (Mar. 2010).
Ramsauer et al., "Chikungunya Virus Vaccines: Viral Vector-Based Approaches," J. Infect. Dis., 214(suppl 5):S500-S505 (Dec. 2016).
Reyes-del Valle et al., "Protective anti-hepatitis B virus responses in rhesus monkeys primed with a vectored measles virus and boosted with a single dose of hepatitis B surface antigen," J. Virol., 83(17):9013-7 (Sep. 2009).
Rodriguez-Freixinos et al., "Current and emerging treatment options in the management of advanced ovarian cancer," Expert Opin. Pharmacother., 17(8):1063-76 (Jun. 2016).
Roy et al., "I-TASSER: a unified platform for automated protein structure and function prediction," Nature Protocols, 5:725-38 (Apr. 2010) doi: 10.1038/nprot.2010.5.
Russell et al., "Measles virus for cancer therapy," Curr. Top. Microbiol. Immunol., 330:213-41 (2009).
Russell et al., "Oncolytic virotherapy," Nat. Biotechnol., 30(7):658-70 (Jul. 2012).
Russell et al., "Tissue-specific and allelic expression of the complement regulator CD46 is controlled by alternative splicing," European Journal of Immunology, 22:1513-1518 (Jun. 1992).
Santiago et al., "Structure of the measles virus hemagglutinin bound to the CD46 receptor," Nature Structural & Molecular Biology, 17:124-9 (Jan. 2010) doi: 10.1038/nsmb.1726.
Schoggins et al., "A diverse range of gene products are effectors of the type I interferon antiviral response," Nature, 472:481-485 (Apr. 2011).
Sisodiya, "Feverish prospects for seizure genetics," Nat Genet, 46:1255-1256 (Dec. 2014).
Skol et al., "Joint analysis is more efficient than replication-based analysis for two-stage genome-wide association studies," Nature Genetics, 38:209-213 (Feb. 2006).
Tan et al., "Twin studies of immunogenicity—determining the genetic contribution to vaccine failure," Vaccine, 19:2434-2439 (Mar. 2001).
Trapnell et al., "TopHat: discovering splice junctions with RNA-Seq," Bioinformatics, 25:1105-11 (May 2009).
Wang et al., "Membrane cofactor protein (MCP; CD46): isoform-specific tyrosine phosphorylation," J. Immunol., 164:1839-1846 (Feb. 2000).
Whitaker et al., "Measles and mumps outbreaks in the United States: Think globally, vaccinate locally," Vaccine, 32:4703-4 (Aug. 2014) doi: 10.1016/j.vaccine.2014.06.088.
Wiltshire et al., "Quantitative trait locus analysis, pathway analysis, and consomic mapping show genetic variants of Tnni3k, Fpgt, or H28 control susceptibility to viral myocarditis," Journal of Immunology, 186:6398-405 (Jun. 2011) doi: 10.4049/jimmunol.1100159.
Wirsching et al., "Glioblastoma," Handb. Clin. Neurol., 134:381-97 (Jan. 2016).
Yang et al., "Protein elastic network models and the ranges of cooperativity," PNAS, 106:12347-52 (Jul. 2009).
Zhao et al., "GLiMMPS: robust statistical model for regulatory variation of alternative splicing using RNA-seq data," Genome biology, 14:R74 (Jul. 2013) doi: 10.1186/gb-2013-14-7-r74.
Zimmermann et al., "MAVENs: motion analysis and visualization of elastic networks and structural ensembles," BMC Bioinformatics, 12:264 (Jun. 2011).
Zuniga et al., "Attenuated measles virus as a vaccine vector," Vaccine, 25(16) 2974 (Apr. 2007).

* cited by examiner

CD46rs2724374

METHODS AND MATERIALS FOR DETECTING SNPS AND ADMINISTERING MEASLES VIRUS VACCINATIONS

CROSS-REFERENCE TO RELATED APPLICATIONS

This application claims the benefit of U.S. Provisional Application Ser. No. 62/464,581, filed Feb. 28, 2017. The disclosure of the prior application is considered part of (and is incorporated by reference in) the disclosure of this application.

STATEMENT AS TO FEDERALLY SPONSORED RESEARCH

This invention was made with government support under AI033144 and AI048793 awarded by National Institutes of Health. The government has certain rights in the invention.

BACKGROUND

1. Technical Field

This document relates to methods and materials involved in using measles viruses. For example, this document provides methods and materials for identifying mammals (e.g., humans) likely to respond to standard measles virus vaccines or standard measles virus-based therapy (e.g., measles virus-based oncolytic therapy or measles virus vectored vaccines). This document also provides methods and materials for identifying mammals (e.g., humans) unlikely to respond to standard measles virus vaccines or standard measles virus-based therapy (e.g., measles virus-based oncolytic therapy or measles virus vectored vaccines).

2. Background Information

Measles remains a disease of public health concern in the developing world and well-developed countries with multiple outbreaks even among populations with high vaccine coverage. From 2010 to date, the European region registered 135,600 measles cases, and the US experienced 1,381 measles cases in 27 states. Several population-based studies estimated that 2 to 10% of vaccine recipients do not develop or sustain measles-specific protective immunity after two doses of MMR vaccine (Bednarczyk et al., *Am. J. Epid.,* 184:148-56 (2016); Haralambieva et al., *Vaccine,* 29:4485-4491 (2011); Haralambieva et al., *Ex. Rev. Vaccines,* 12:57-70 (2013); Poland and Jacobson, *Vaccine,* 30:103-104 (2012); and Whitaker and Poland, *Vaccine,* 32:4703-4704 (2014)). The mechanisms behind vaccine failure are unknown.

SUMMARY

This document provides methods and materials involved in using measles viruses. For example, this document provides methods and materials for identifying mammals (e.g., humans) likely to respond to standard measles virus vaccines or measles virus-based therapies (e.g., oncolytic measles virus-based therapies). As described herein, a human identified as having the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, the minor allele C of CD46 rs11806810, or combinations thereof can be classified as being a human who is more likely to favorably respond to standard measles virus vaccination protocols and/or measles virus-based therapies (e.g., oncolytic measles virus-based therapies). In some cases, such identified humans can be administered a standard measles virus vaccination protocol when undergoing measles virus vaccination or a measles virus-based therapy (e.g., an oncolytic measles virus-based therapy) when being treated for cancer or other conditions.

This document also provides methods and materials for identifying mammals (e.g., humans) that are less likely to respond to standard measles virus vaccines or measles virus-based therapies (e.g., oncolytic measles virus-based therapies). As described herein, a human identified as having the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, the major allele G of CD46 rs11806810 or combinations thereof can be classified as being a human who is less likely to favorably respond to standard measles virus vaccination protocols and/or measles virus-based therapies (e.g., oncolytic measles virus-based therapies). In some cases, humans identified as having two or more of the minor alleles listed in this paragraph (e.g., a homozygous minor allele genotype) can be less likely to favorably respond to standard measles virus vaccination protocols and/or measles virus-based therapies (e.g., oncolytic measles virus-based therapies). In some cases, such identified humans can be administered an enhanced measles virus vaccination protocol (e.g., different dosage, number of doses, route of vaccination, and/or modified vaccine formulation) when undergoing measles virus vaccination or a modified measles virus-based therapy or treatment (e.g., non-measles virus-based cancer therapy in the case when measles virus-based oncolytic therapy is considered as a treatment option). Examples of such other treatments include, without limitation, other non-measles oncolytic virotherapy agents (e.g., adenovirus, Herpes simplex virus, poliovirus, parvovirus, reovirus, New Castle virus, Coxsackie virus, or vaccinia) as described elsewhere (Russell et al., *Nat. Biotechnol.,* 30(7):658-70 (2012) and targeted cancer therapy or standard chemotherapy treatments for specific cancers/malignancies such as those described elsewhere (Mikhael et al., *Mayo Clin. Proc.,* 88(7):777 (2013); Dispenzieri et al., *Blood,* 122(26):4172-81 (2013); Aletti et al., *Mayo Clin. Proc.,* 82(6):751-70 (2007); Grunewald et al., *Best Pract Res. Clin. Obstet. Gynaecol.*, pii: S1521-6934(16)30142-0 (2016); Rodriguez-Freixinos et al., *Expert Opin. Pharmacother.,* 17(8):1063-76 (2016); Hans-Georg Wirsching et al., *Handb. Clin. Neurol.,* 134:381-97 (2016); and Johnson et al., *Semin. Oncol.,* 41(4):511-22 (2014)).

In general, one aspect of this document features a method for identifying a human as being likely to respond to a measles virus vaccination. The method comprises, or consists essentially of, (a) detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, or the minor allele C of CD46 rs11806810 in a sample obtained from the human, and (b) classifying the human as being likely to respond to the measles virus vaccination. The method can comprise detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 in the sample. The measles virus vaccination can be a measles, mumps, and rubella vaccine.

In another aspect, this document features a method for providing a human with a measles virus vaccination. The method comprises, or consists essentially of, (a) detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, or the minor allele C of CD46 rs11806810 in a sample obtained from the human, and (b) administering a measles virus vaccine to the human. The method can comprise detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 in the sample. The measles virus vaccine is a measles, mumps, and rubella vaccine.

In another aspect, this document features a method for identifying a human as being unlikely to respond to a measles virus vaccination. The method comprises, or consists essentially of, (a) detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, or the major allele G of CD46 rs11806810 in a sample obtained from the human, and (b) classifying the human as being unlikely to respond to the measles virus vaccination. The method can comprise detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 in the sample. The measles virus vaccination is a measles, mumps, and rubella vaccine.

In another aspect, this document features a method for providing a human with a measles virus vaccination. The method comprises, or consists essentially of, (a) detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, or the major allele G of CD46 rs11806810 in a sample obtained from the human, and (b) administering an enhanced measles virus vaccine to the human or administering a measles virus vaccine at least three times to the human. The method can comprise detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 in the sample. The method can comprises administering the enhanced measles virus vaccine, and wherein the enhanced measles virus vaccine comprises adjuvants having the ability to increase surface expression of CD46 or upregulation of IFI44L. The method can comprises administering the measles virus vaccine, and the measles virus vaccine can be a measles, mumps, and rubella vaccine.

In another aspect, this document features a method for identifying a human having cancer (or other condition requiring measles virus-based therapy) as being likely to respond to a measles virus-based therapy. The method comprises, or consists essentially of, (a) detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, or the minor allele C of CD46 rs11806810 in a sample obtained from the human, and (b) classifying the human as being likely to respond to the measles virus-based oncolytic treatment. The method can comprise detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 in the sample.

In another aspect, this document features a method for treating a human having cancer. The method comprises, or consists essentially of, (a) detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, or the minor allele C of CD46 rs11806810 in a sample obtained from the human, and (b) administering a measles virus-based oncolytic treatment to the human. The method can comprise detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 in the sample.

In another aspect, this document features a method for identifying a human having cancer as being unlikely to respond to a measles virus-based oncolytic treatment. The method comprises, or consists essentially of, (a) detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, or the major allele G of CD46 rs11806810 in a sample obtained from the human, and (b) classifying the human as being unlikely to respond to the measles virus-based oncolytic treatment. The method can comprise detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 in the sample.

In another aspect, this document features a method for treating a human having cancer. The method comprises, or consists essentially of, (a) detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, or the major allele G of CD46 rs11806810 in a sample obtained from the human, and (b) administering a modified measles virus-based oncolytic treatment or a non-measles virus-based oncolytic treatment to the human. The method can comprise detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 in the sample.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1A:
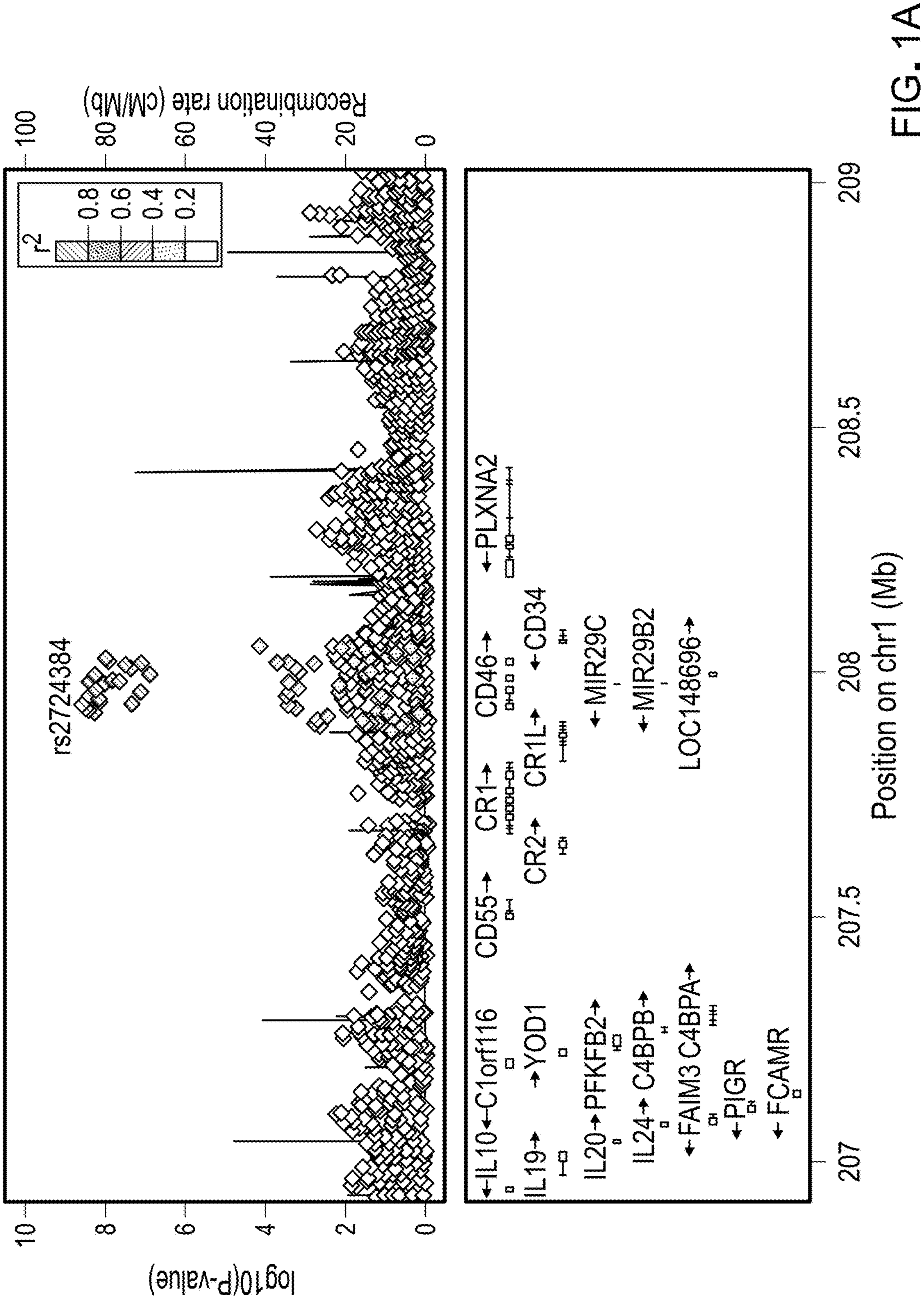
FIGS. 1A-1D. Locus zoom plots of the chromosome 1 regions and effects of SNPs associated with measles-specific neutralizing antibody titers in the combined cohort. (A and C) Locus zoom plots of the 1q32 (CD46, A) and 1q31.1 (IFI44L, C) regions associated with neutralizing antibody titer after measles vaccination. On the x-axis, SNPs are plotted by chromosomal location. The left y-axis reflects the association ($-\log_{10}$ P-value) with vaccine-induced measles-specific antibody titer, while the right y-axis reflects recombination rates and LD ($r^2$ color) of each plotted SNP with the most significant SNP (designated by a black diamond). (B and D) Effect of top two CD46 SNPs (B) and IFI44L SNPs (D) on measles-specific antibody response (effect in the combined cohort is presented as Turkey box-and-whisker plots). On the x-axis, 0 designates subjects with homozygous major allele genotype, 1 designates heterozygous subjects, and 2 designates subjects with homozygous minor allele genotype. On the y-axis, neutralizing antibody titer is presented as the natural log of the PRMN mIU/mL value. The top (bottom) of the box indicates the 75th (25th) percentiles, respectively, while the bold line within the box indicates the median, and the whiskers indicate 1.5 times the IQR (n=2872; reduced to 2818 after excluding subjects with immune outcome data that failed QC).
Figure 1B:
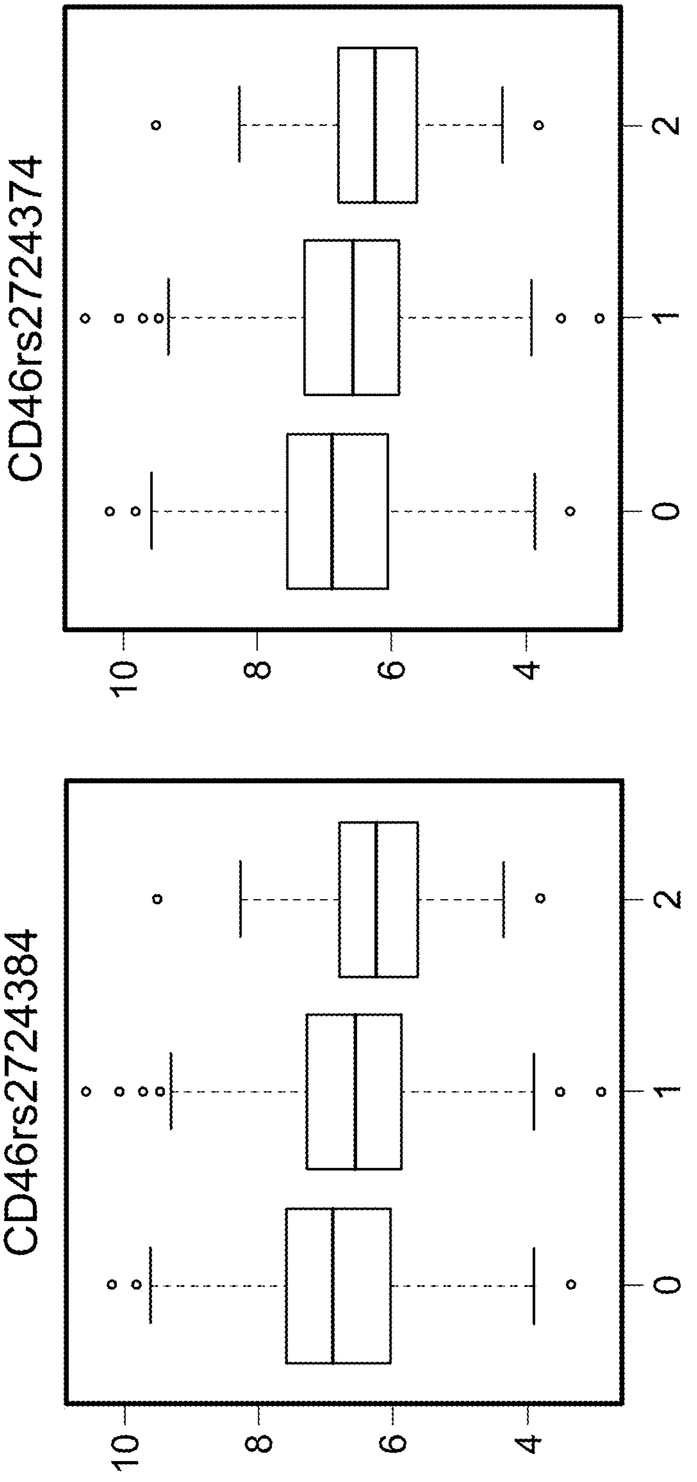
Figure 1C:
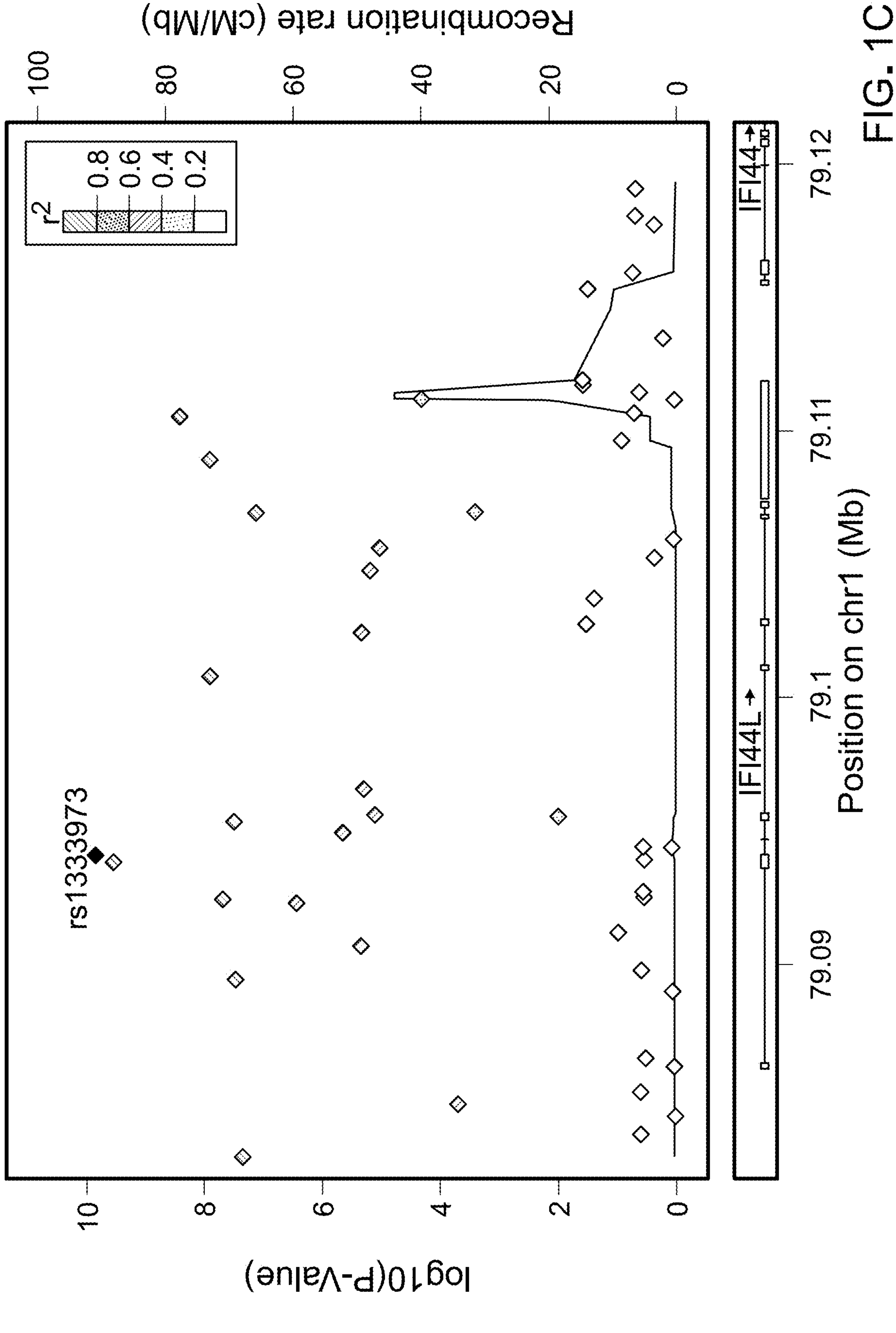
Figure 1D:
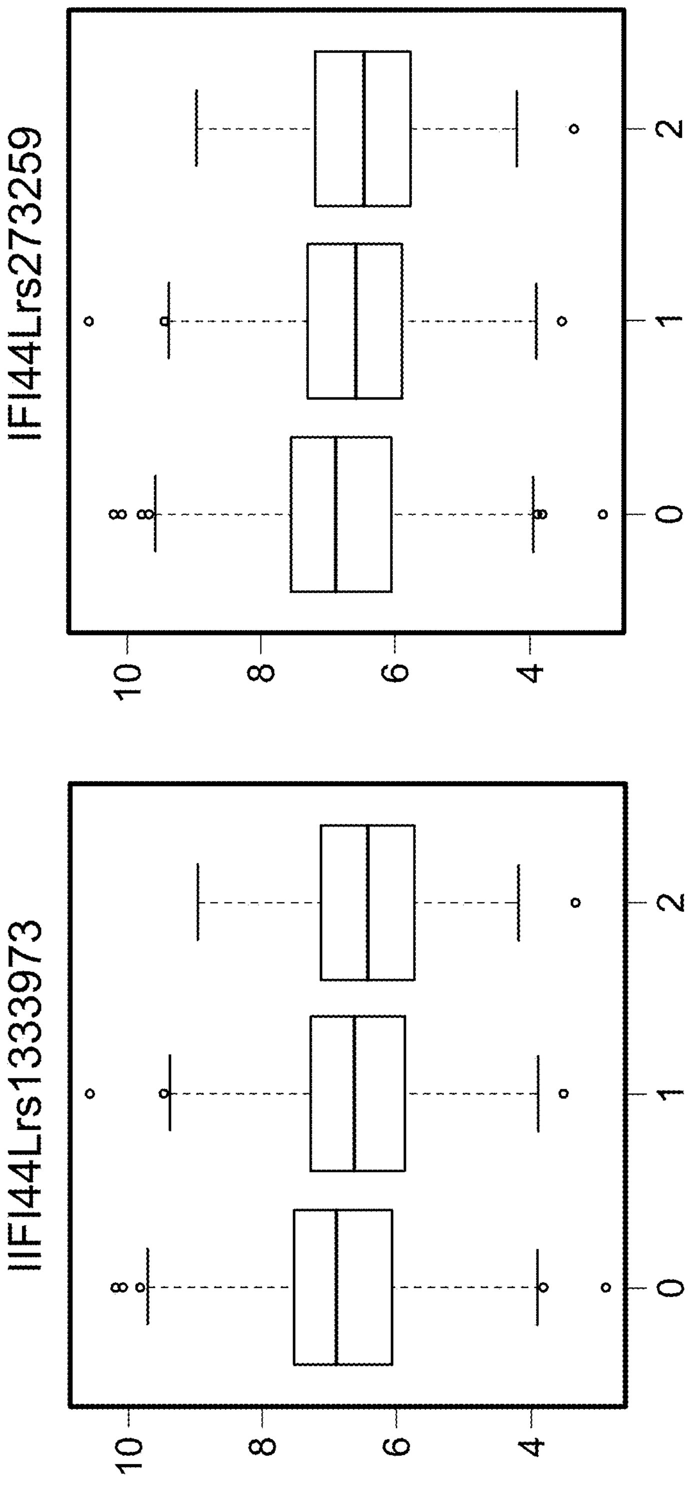

This document provides methods and materials involved in using measles viruses. For example, this document provides methods and materials for identifying mammals (e.g., humans) likely to respond to standard measles virus vaccines or standard measles virus-based oncolytic treatments. As described herein, a human identified as having the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, the minor allele C of CD46 rs11806810, or combinations thereof can be classified as being a human who is more likely to favorably respond to standard measles virus vaccination protocols and/or measles virus-based therapies (e.g., oncolytic measles virus-based therapies). Examples of such therapies and treatments include, without limitation, those involving the use of measles viruses as a vaccine vector as described elsewhere (Zuniga et al., *Vaccine,* 25(16) 2974 (2007); Reyes-del Valle et al., *J. Virol.,* 83(17):9013-7 (2009); Harahap-Carrillo et al., *Vaccines* (Basel), 3(3):50 (2015); Brandler et al., *Vaccine,* 28(41):6730 (2010); Ramsauer et al., *J. Infect. Dis.,* 214 (suppl 5):S500-S505 (2016); Elsedawy et al., *Expert Rev. Vaccines.,* 12(10):115 (2013); Russell et al., *Nat. Biotechnol.,* 30(7):658 (2012); Lech et al., *Expert Rev. Vaccines,* 9(11):1275 (2010); Russell et al., *Curr. Top. Microbiol. Immunol.,* 330:21 (2009); Msaouel et al., *Expert Opin. Biol. Ther.,* 13(4):483 (2013); and Msaouel et al., *Curr. Pharm. Biotechnol.,* 13(9):1732 (2012)). In some cases, humans identified as having two or more of the major alleles listed in this paragraph (e.g., homozygous major allele genotype) are more likely to favorably respond to standard measles virus vaccination protocols and/or measles virus-based therapies. In some cases, such identified humans can be administered a standard measles virus vaccination protocol when undergoing measles virus vaccination or a measles virus-based therapy.

Examples of standard measles virus vaccination protocols that can be used when vaccinating a human identified as described herein include, without limitation, administering two doses of a measles-containing vaccine in a life time. Any appropriate measles virus-based oncolytic treatment or other measles virus-based therapy/treatment can be used when treating cancer (or other condition) in a human identified as being a favorable responder as described herein. Examples of measles virus-based oncolytic treatments that can be used as described herein include, without limitation, those described elsewhere (Elsedawy et al., *Expert Rev. Vaccines.,* 12(10):115 (2013); Russell et al., *Nat. Biotechnol.,* 30(7):658 (2012); Lech et al., *Expert Rev. Vaccines,* 9(11):1275 (2010); Russell et al., *Curr. Top. Microbiol. Immunol.,* 330:21 (2009); Msaouel et al., *Expert Opin. Biol. Ther.,* 13(4):483 (2013); and Msaouel et al., *Curr. Pharm. Biotechnol.,* 13(9):1732 (2012)). Measles virus-based oncolytic therapy can be used in a human identified as being a favorable responder as described herein.

Any appropriate cancer can be treated using a measles virus-based oncolytic treatment in a human identified as being a favorable responder as described herein including, without limitation, Hodgkin's disease, Burkitt's lymphoma, multiple myeloma, ovarian cancer, colorectal cancer, breast cancer, lymphoma, leukemia, thyroid cancer, ovarian cancer, liver cancer, prostate cancer, mesothelioma, melanoma, renal cell carcinoma, fibrosarcoma, hepatocellular carcinoma, medulloblastoma, head and neck squamous cell cancer, rhabdomyosarcoma, and glioma (see, e.g., Russell et al., *Curr. Top. Microbiol. Immunol.,* 330:213 (2009); Blechacz et al., *Hepatology.* 44(6):1465-77 (2006); and Russell et al., *Nat. Biotechnol.,* 30(7):658 (2012).

In some cases, the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 can be used in combination to identify a human who is more likely to favorably respond to standard measles virus vaccination protocols and/or measles virus-based therapies (e.g., oncolytic measles virus-based therapies).

This document also provides methods and materials for identifying mammals (e.g., humans) unlikely to respond to standard measles virus vaccines or standard measles virus-based oncolytic treatments. As described herein, a human identified as having the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, the major allele G of CD46 rs11806810, or combinations thereof can be classified as being a human who is less likely to favorably respond (and/or more likely to not favorably respond) to standard measles virus vaccination protocols and/or measles virus-based therapies (e.g., oncolytic measles virus-based therapies) such as those therapies/treatments using measles virus as a vaccine vector as described elsewhere (Zuniga et al., *Vaccine,* 25(16) 2974 (2007); Reyes-del Valle et al., *J. Virol.,* 83(17):9013-7 (2009); Harahap-Carrillo et al., Vaccines (Basel), 3(3):50 (2015); Brandler et al., *Vaccine,* 28(41):6730 (2010); Ramsauer et al., *Infect. Dis.,* 214 (suppl 5):S500-S505 (2016); Elsedawy et al., *Expert Rev. Vaccines.,* 12(10):115 (2013); Russell et al., *Nat. Biotechnol.,* 30(7):658 (2012); Lech et al., *Expert Rev. Vaccines,* 9(11):1275 (2010); Russell et al., *Curr. Top. Microbiol. Immunol.,* 330:21 (2009); Msaouel et al., *Expert Opin. Biol. Ther.,* 13(4):483 (2013); and Msaouel et al., *Curr. Pharm. Biotechnol.,* 13(9):1732 (2012)). In some cases, humans identified as having two of the minor alleles listed in this paragraph (e.g., homozygous minor allele genotype) can be less likely to favorably respond (e.g., more likely to not favorably respond) to standard measles virus vaccination protocols and/or measles virus-based therapies. In some cases, such identified humans can be administered an enhanced measles virus vaccination protocol when undergoing measles virus vaccination or a modified measles virus-based therapy (or non-measles virus-based therapy or oncolytic treatment in cancer) when being treated for cancer or other conditions. Examples of enhanced measles virus vaccination protocols that can be used when vaccinating a human identified as being unlikely to respond to standard measles virus vaccination protocols as described herein include, without limitation, increased dosage or number of doses, different route of immunization (e.g., intranasal, where the virus could preferentially use other receptors), modified vaccine formulation (e.g., adjuvants boosting surface expression of CD46 and/or upregulation of IFI44L), modified measles vaccine virus with equivalent or enhanced ability to infect the CD46 variant expressed by low responders or modified measles vaccine virus using exclusively other natural entry receptors such as SLAM or Nectin-4 (PVRL4) or measles virus artificially retargeted to other cellular ligands/receptors as described elsewhere (Aref et al., *Viruses,* 8(10) pii:E294 (2016); and Lin and Richardson, *Viruses,* 8(9) pii:E250 (2016)). Any appropriate modified measles virus-based therapy (or virus-based oncolytic therapy in the case of malignancies) or non-measles virus-based therapy can be used when treating cancer or other conditions in a human identified as being less likely to respond to measles virus-based therapy as described herein. Examples of measles virus-based oncolytic treatments include, without limitation, those in advanced stage of clinical research and undergoing clinical trials (see, e.g., Elsedawy et al., *Expert Rev. Vaccines.,* 12(10):115 (2013); Russell et al., *Nat. Biotechnol.,* 30(7):658 (2012); Lech et al., *Expert Rev. Vaccines,* 9(11):1275 (2010); Russell et al., *Curr. Top. Microbiol. Immunol.,* 330:21 (2009); Msaouel et al., *Expert Opin. Biol. Ther.,* 13(4):483 (2013); and Msaouel et al., *Curr. Pharm. Biotechnol.,* 13(9):1732 (2012)). Any appropriate cancer can be treated using a modified and/or enhanced measles virus-based oncolytic treatment or non-measles virus-based oncolytic treatment in a human identified as being less likely to respond to measles virus-based therapy/treatment as described herein including, without limitation, Hodgkin's disease, Burkitt's lymphoma, multiple myeloma, ovarian cancer, colorectal cancer, breast cancer, lymphoma, leukemia, thyroid cancer, ovarian cancer, liver cancer, prostate cancer, mesothelioma, melanoma, renal cell carcinoma, fibrosarcoma, hepatocellular carcinoma, medulloblastoma, head and neck squamous cell cancer, fibrosarcoma, rhabsomyosarcoma, and glioma.

In some cases, the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 can be used in combination to identify a human who is less likely to favorably respond (and/or more likely to not favorably respond) to respond to standard measles virus vaccination protocols and/or measles virus-based therapies.

Any appropriate method can be used to determine the presence or absence of particular alleles for the SNP positions provided herein. For example, nucleic acid sequencing techniques such as Sanger sequencing or next generation sequencing can be used to identify which nucleotides are present at the SNP locations identified herein. In some cases, SNP detection techniques can be used to identify which nucleotides are present at the SNP locations identified herein.

The invention will be further described in the following examples, which do not limit the scope of the invention described in the claims.

EXAMPLES

Example 1—Genome-Wide Associations of CD46 and IFI44L Genetic Variants with Neutralizing Antibody Response to Measles Vaccine Study Subjects A large sample of 3,191 healthy children, older adolescents, and healthy adults (age 11 to 40 years) consisting of three independent cohorts were analyzed: a Rochester cohort (n=1,062); a San Diego cohort (n=1,071); and a US cohort (n=1,058). The demographic and clinical characteristics of these cohorts are described elsewhere (Haralambieva et al., *Vaccine,* 29:7883-7895 (2011); Haralambieva et al., *Vaccine,* 29:8988-8997 (2011); Kennedy et al., *Vaccine,* 30:2159-2167 (2012); Kennedy et al., *Human Genetics,* 131:1433-1451 (2012); Kennedy et al., *Human Genetics,* 131:1403-1421 (2012); Lambert et al., *J. Infect. Dis.,* 211:898-905 (2015); Ovsyannikova et al., *Human Heredity,* 72:206-223 (2011); Ovsyannikova et al., *Human Genetics,* 130:547-561 (2011); and Ovsyannikova et al., *Vaccine,* 30:2146-2152 (2012)).

The Rochester cohort comprised 1,062 individuals enrolled into three age-stratified cohorts of healthy, school-age children and young adults from all socioeconomic strata in Rochester, Minn., recruited between 2001-2009. Each subject had written records of having received two doses of MMR vaccine. Of the 1,062 individuals for this study, 982 (93%) were successfully genotyped and assayed for immune outcomes.

The San Diego cohort consisted of 1,071 healthy older adolescents and healthy adults (age 18 to 40 years) from armed forces personnel in San Diego, Calif., enrolled by the US Naval Health Research Center (NHRC) between 2005-2006. The US cohort consisted of an additional 1,058 healthy older adolescents and healthy adults recruited from the US armed forces, enrolled between 2010-2011. Of the 1,071 and 1,058 subjects recruited into this study as the San Diego or US cohort (respectively), 882 (82%) subjects for the San Diego cohort and 1,008 (95%) subjects for the US cohort had provided consent for use of their samples/data in other studies, and were successfully genotyped and assayed for measles-specific immune outcomes for this study.

Genotyping and Immune Outcomes

The genome-wide SNP typing was performed using the Infinium Omni 1M-Quad SNP array (Illumina; San Diego, Calif.) for the Rochester cohort, Illumina Human Omni2.5-8 BeadChip array for the US cohort, and Illumina Infinium HumanHap550v3_A or HumanHap650Yv3 BeadChip arrays for the San Diego cohort. Measles-specific neutralizing antibody and cytokine responses were quantified using a fluorescence-based plaque reduction microneutralization assay (PRMN) and ELISPOT/ELISA assays as described elsewhere (Haralambieva et al., *Vaccine,* 29:4485-4491 (2011)). The humoral immune response phenotype, the 50% end-point titer (Neutralizing Dose, ND50), was calculated using Karber's formula and transformed into mIU/mL (using the 3rd WHO international measles antibody standard), as described elsewhere (Haralambieva et al., *Vaccine,* 29:4485-4491 (2011)). The variability of the PRMN assay, calculated as a coefficient of variation (CV) based on the log-transformed ND50 values of the third WHO standard, was 5.7%, as described elsewhere (Haralambieva et al., *Vaccine,* 29:4485-4491 (2011)).

Briefly, DNA was extracted from each subject's blood specimen using the Gentra Puregene Blood kit (Gentra Systems Inc.; Minneapolis, Minn.) and quantified by Picogreen (Molecular Probes; Carlsbad, Calif.). The genome-wide SNP typing was performed using the Infinium Omni 1M-Quad SNP array (Illumina; San Diego, Calif.) for the Rochester cohort, Illumina Human Omni2.5-8 BeadChip array for the US cohort, and Illumina Infinium HumanHap550v3_A or HumanHap650Yv3 BeadChip arrays for the San Diego cohort. DNA samples underwent amplification, fragmentation, and hybridization onto each BeadChip, which were imaged on an Illumina BeadArray reader. Genotype calls based on clustering of the raw intensity data were made using BeadStudio 2 software.

For the 758 subjects in the San Diego cohort with the Illumina 550 array genotyping data, 54 subjects were removed due to high SNP missing rates (more than 5% of their SNPs missing). There were 561,303 unique measured SNPs, of which 508,199 SNPs passed QC. For the 313 subjects in the San Diego cohort with the Illumina 650 array genotyping data, 13 subjects were removed due to high SNP missing rates. There were 660,755 unique measured SNPs, of which 630,240 passed QC. In addition, subjects were further excluded from the San Diego cohort if not of Caucasian or African-American ancestry (determined by STRUCTURE), or if they were missing values for covariates used in the analysis. This resulted in a total of 882 subjects from this cohort used in the study (718 Caucasians and 164 African-Americans, see Table 1). For the 1,058 subjects in the US cohort with the Illumina Omni 2.5 array genotyping data, there were 2,376,105 measured SNPs, of which 2,116,447 passed QC. Subjects were excluded from the US cohort if not of Caucasian or African-American ancestry as determined by STRUCTURE, or had high SNP missing rates, or if values for covariates were missing; this resulted in a total of 1,008 subjects (895 Caucasians and 113 African Americans, Table 1). For the 1,062 subjects in the Rochester cohort with valid data, 10 subjects were removed due to high SNP missing rates. Subjects were further excluded from the cohort if not of Caucasian or African-American ancestry determined by STRUCTURE, or if values for covariates were missing; this resulted in a total of 982 subjects (942 Caucasians and 40 African Americans, Table 1). On the Omni 1 genotyping array, there were 1,134,514 unique measured SNPs, of which 887,889 passed QC.

TABLE 1

Demographic and immune characterization of the study population

| | African American[e] (n = 317) | Caucasian[e] (n = 2555) | Total (n = 2872) | P-value |
|---|---|---|---|---|
| Neutralizing Ab titer[a] | | | | <0.001[f] |
| N missing (failed assay QC) | 5 | 49 | 54 | |
| Mean (SD[c]) | 2065 (2821) | 1271 (1652) | 1359 (1835) | |
| Median (IQR[d]) | 1180 (550, 2632) | 803 (383, 1607) | 845 (394, 1683) | |
| IFNγ ELISPOT response[b] | | | | 0.427[f] |
| N missing (failed assay QC) | 26 | 228 | 254 | |
| Mean (SD[c]) | 24.4 (26) | 25.2 (32) | 25.1 (31.4) | |
| Median (IQR[d]) | 15 (7, 34.5) | 15 (6, 32.5) | 15 (6, 32.7) | |
| Gender/sex | | | | 0.082[g] |
| Female | 73 (23%) | 707 (27.7%) | 780 (27.2%) | |
| Male | 244 (77%) | 1848 (72.3%) | 2092 (72.8%) | |
| Race (self-declared) | | | | NA[h] |
| White | 0 (0%) | 2206 (86.3%) | 2206 (76.8%) | |
| Black or African American | 302 (95.3%) | 38 (1.49%) | 340 (11.8%) | |
| American Indian/Alaska Native | 0 (0%) | 29 (1.14%) | 29 (1.01%) | |
| Asian/Hawaiian/Pacific Islander | 1 (0.315%) | 19 (0.744%) | 20 (0.696%) | |
| Multiple | 9 (2.84%) | 100 (3.91%) | 109 (3.8%) | |
| Other | 4 (1.26%) | 119 (4.66%) | 123 (4.28%) | |
| Unknown | 1 (0.315%) | 44 (1.72%) | 45 (1.57%) | |
| Ethnicity (self-declared) | | | | <0.001[g] |
| Hispanic/Latino | 13 (4.1%) | 387 (15.1%) | 400 (13.9%) | |
| Not Hispanic/Latino | 285 (89.9%) | 2137 (83.6%) | 2422 (84.3%) | |
| Unknown | 19 (5.99%) | 31 (1.21%) | 50 (1.74%) | |
| Age at enrollment (years) | | | | <0.001[f] |
| Number missing | 49 | 196 | 245 | |
| Mean (SD[c]) | 24.5 (5.97) | 21.1 (6.06) | 21.4 (6.14) | |
| Median (IQR[d]) | 24 (21, 28) | 22 (16, 25) | 22 (16, 25) | |
| Age at last vaccination (years) | | | | <0.001[f] |
| Number missing | 107 | 577 | 684 | |
| Mean (SD[c]) | 19.8 (7.97) | 16.1 (8.38) | 16.4 (8.41) | |
| Median (IQR[d]) | 20 (18, 24) | 18 (10, 22) | 18 (11, 23) | |
| Time from last vaccination to enrollment (years) | | | | 0.031[f] |

TABLE 1-continued

Demographic and immune characterization of the study population

| | African American[e] (n = 317) | Caucasian[e] (n = 2555) | Total (n = 2872) | P-value |
|---|---|---|---|---|
| Number missing | 107 | 577 | 684 | |
| Mean (SD[c]) | 3.7 (3.85) | 4.0 (3.43) | 4.0 (3.47) | |
| Median (IQR[d]) | 2.6 (0.04, 5.5) | 3.5 (0.03, 6.4) | 3.4 (0.03, 6.4) | |
| Cohort | | | | <0.001[g] |
| Rochester | 40 (12.6%) | 942 (36.9%) | 982 (34.2%) | |
| San Diego | 164 (51.7%) | 718 (28.1%) | 882 (30.7%) | |
| US | 113 (35.6%) | 895 (35%) | 1008 (35.1%) | |

[a]Neutralizing antibody titer in mIU/mL, measured by the plaque reduction microneutralization assay (PRMN)
[b]IFNγ-positive spot-forming units (SFUs) per 2 × $10^5$ cells (mean of measles virus-specific stimulated response, measured in triplicate, minus the mean unstimulated response, also measured in triplicate).
[c]Standard Deviation.
[d]IQR, inter-quartile range with 25% and 75% quartiles
[e]Genetically classified into African American or Caucasian ancestry group based on STRUCTURE (see Methods)
[f]Kruskal-Wallis Rank Test
[g]Fisher's Exact Test
[h]Not applicable Next Generation Sequencing (mRNA-Seq)

Libraries were generated from total RNA (extracted from PBMCs of 30 subjects) using Illumina's mRNA TruSeq (vi) kit and sequenced (paired end sequencing) on an Illumina HiSeq 2000 (Illumina; San Diego, Calif.) with Illumina's TruSeq Cluster kit (v3-cBot-HS) and 51 Cycle Illumina TruSeq SBS Sequencing Kit (v3), as described elsewhere (Haralambieva et al., *PLos ONE,* 11:e0160970 (2016)).

Briefly, cryopreserved PBMCs from 30 Rochester cohort subjects (selected for an mRNA-Seq transcriptome profiling, based on their neutralizing antibody titers (15 highest and 15 lowest antibody responders) after two doses of MMR vaccine) were thawed and stimulated with live Edmonston measles virus (MV) at a multiplicity of infection (MOI) of 0.5 for 24 hours (for each subject, an aliquot of the cells was left unstimulated). The samples were randomly allocated to flow cells and lanes, balancing over the immune response and stimulation status.

Cells were stabilized with RNAprotect cell reagent (Qiagen) and total RNA was extracted using RNeasy Plus mini kit (Qiagen). Quality and quantity of RNA was determined by Nanodrop spectrophotometry (Thermo Fisher Scientific). Libraries were generated using Illumina's mRNA TruSeq (v1) kit and sequenced (paired end sequencing) on an Illumina HiSeq 2000 (Illumina; San Diego, Calif.) with Illumina's TruSeq Cluster kit (v3-cBot-HS) and 51 Cycle Illumina TruSeq SBS Sequencing Kit (v3). The sequencing reads were aligned to the human genome build 37.1 using TopHat (1.3.3) and Bowtie (0.12.7). Gene counts were performed using HTSeq (0.5.3p3), while BEDTools software (2.7.1) was used to map normalized read count to individual exons (Langmead et al., *Genome Biol.,* 10:R25 (2009); Quinlan et al., *Bioinformatics,* 26:841-2 (2010); Trapnell et al., *Bioinformatics,* 25:1105-11 (2009); and Anders et al., *Bioinformatics,* 31:166-9 (2015)).

RT-PCR

One-Step RT-PCR system with Platinum Taq® DNA polymerase (Invitrogen, Carlsbad, Calif.) and primers allowing CD46 isoform/isoforms discrimination were used as described elsewhere (Wang et al., *J. Immunol.,* 164:1839-1846 (2000)). Briefly, total RNA was extracted from PBMCs of 30 subjects (10 CD46 rs2724374 homozygous major allele genotype subjects, 10 rs2724374 homozygous minor allele genotype subjects and 10 heterozygous subjects) using RNAprotect cell reagent and the RNAeasy Plus Mini kit (Qiagen, Valencia, Calif.). RT-PCR analysis of CD46 isoforms was performed with the SuperScript One-Step RT-PCR system with Platinum Taq DNA polymerase (Invitrogen, Carlsbad, Calif.), as described elsewhere (Wang et al., *J. Immunol.,* 164:1839-1846 (2000)) using the 5' CD46 SCR4 primer GTGGTCAAATGTCGATTTCCAG-TAGTCG (SEQ ID NO:1) and the 3' untranslated region primer CAAGCCACATTGCAATATTAGCTAAGCCACA (SEQ ID NO:2), allowing CD46 isoform/isoforms discrimination/separation on a 3% agarose gel.

Immune Outcome Phenotyping

The immune outcome assays described herein were similar or identical to those described elsewhere (Kennedy et al., *Vaccine,* 30:2159-2167 (2012); Ovsyannikova et al., *Human Genetics,* 130:547-561 (2011); Ovsyannikova et al., *Human Heredity,* 72:206-223 (2011); Haralambieva et al., *Vaccine,* 29:8988-8997 (2011); Haralambieva et al., *Vaccine,* 29:7883-7895 (2011); Ovsyannikova et al., *Vaccine,* 30:4182-4189 (2012); Haralambieva et al., *Vaccine,* 29:4485-4491 (2011); and Ovsyannikova et al., *Human Genetics,* 133:1083-92 (2014)).

Neutralizing Antibody Assay

Measles-specific neutralizing antibody titers were quantified using a high-throughput, fluorescence-based plaque reduction microneutralization assay (PRMN), using a recombinant GFP-expressing measles virus as described elsewhere (Ovsyannikova et al., *Human Heredity,* 72:206-223 (2011); Haralambieva et al., *Vaccine,* 29:8988-8997 (2011); Haralambieva et al., *Vaccine,* 29:7883-7895 (2011); Ovsyannikova et al., *Vaccine,* 30:4182-4189 (2012); Haralambieva et al., *Vaccine,* 29:4485-4491 (2011); and Ovsyannikova et al., *Human Genetics,* 133:1083-92 (2014)). The plates were scanned and counted on an automated Olympus IX71 Fluorescent microscope using the Image-Pro Plus Software Version 6.3 (MediaCybernetics). The 50% endpoint titer (Neutralizing Doze, ND50) was calculated automatically using Karber's formula, and transformed into mIU/mL (using the 3rd WHO international anti-measles antibody standard), as described elsewhere (Ovsyannikova et al., *Human Heredity,* 72:206-223 (2011); Haralambieva et al., *Vaccine,* 29:8988-8997 (2011); Haralambieva et al., *Vaccine,* 29:7883-7895 (2011); Ovsyannikova et al., *Vaccine,* 30:4182-4189 (2012); Haralambieva et al., *Vaccine,* 29:4485-4491 (2011); and Ovsyannikova et al., *Human Genetics,* 133:1083-92 (2014)). The variability of the PRMN assay, calculated as a coefficient of variation (CV) based on the log-transformed ND50 values of the third WHO standard, was 5.7% (Haralambieva et al., *Vaccine,* 29:4485-4491 (2011)).

IFNγ ELISPOT Assay

Measles-specific cellular immunity was quantified using commercial Human IFNγ ELISPOT kits (R&D Systems; Minneapolis, Minn.) to measure the number of MV-specific IFNγ-producing cells, according to the manufacturer's instructions and as described elsewhere (Ovsyannikova et al., *Pharmacogenet. Genomics,* 22:20-31 (2012)). Subjects' peripheral blood mononuclear cells/PBMCs were stimulated (or, alternatively, unstimulated) in triplicate with the Edmonston strain of MV (MOI=0.5), and developed the reaction after 42 hours incubation at 37° C., in 5% $CO_2$. PHA (5 μg/mL) was used as a positive control. All plates were scanned and analyzed using the same counting parameters on an ImmunoSpot S4 Pro Analyzer (Cellular Technology Ltd.; Cleveland, Ohio) using ImmunoSpot version 4.0 software (Cellular Technology Ltd.). The ELISPOT response was presented in spot-forming units (SFUs) per $2\times10^5$ cells. The intraclass correlation coefficients, comparing multiple observations per sample (stimulated and unstimulated condition), was 0.94 for the stimulated values and 0.85 for the unstimulated values, indicating low assay variability.

Measles-Specific Secreted Cytokines

Secreted cytokines (IL-2, IL-6; IL-10; TNFα, IFNγ, IFNα, and IFNλ1) were quantified in PBMC cultures after in vitro stimulation with live MV, as described elsewhere (Ovsyannikova et al., *Human Heredity,* 72:206-223 (2011); Haralambieva et al., *Vaccine,* 29:8988-8997 (2011); and Haralambieva et al., *Vaccine,* 29:7883-7895 (2011)).

Statistical Methods

GWAS Analysis

To achieve greatest power to detect SNPs associated with measles-specific immune response phenotypes, data were pooled across genotyping platforms and the three cohorts. To perform the pooled analyses, the effects of potentially confounding factors that vary across ancestry/platform/cohort strata were first accounted for. After thoroughly evaluating the quality of the genotype data, the genetic data were used to define major ancestry groups. Eigenvectors within each ancestry group were then estimated to account for the effects of population stratification within ancestry groups. Because the largest ancestry groups were Caucasian and African-American, pooled analysis was restricted to these groups. After accounting for population stratification, the covariates that were available within each of the ancestry-platform-cohort strata were evaluated to determine if the covariates were associated with the phenotype, in order to regress out the effects of potential confounding factors. This produced residuals (adjusted traits) that were then used for the GWAS analyses. The immune response trait measles-specific IFNγ ELISPOT, as well as measles-specific secreted cytokines, were transformed by normal quantiles of the difference of the mean stimulated and mean unstimulated values. The immune response trait neutralizing antibody titer was transformed as the natural log of the PRMN mIU/mL value.

Genotype Quality Control and Imputation

Genotype quality control prior to imputation was conducted separately for four strata: subjects in the San Diego cohort with the Illumina 550 array genotyping data; subjects in the San Diego cohort with the Illumina 650 array genotyping data; subjects in the US cohort with the Omni 2.5 array genotyping data; and subjects in the Rochester cohort with the Omni 1M-Quad array genotyping data. SNPs on the Y chromosome and mitochondria were removed, and SNPs were eliminated if they were monomorphic or had a missing rate of 1% (5% for the HumanHap550/650 arrays) or more. Subjects were eliminated if they had more than 5% of their SNPs missing (for the HumanHap550/650 arrays) or more than 1% missing (for the Omni 2.5 and Omni 1M-Quad arrays). The 1000 Genomes cosmopolitan samples (African, AFR; AMR; Asian, ASN; European, EUR) were used as a reference for imputation and were based on Build 37. SNPs that could not be converted to Build 37, or mapped to more than one position, or could not have their alleles verified for the forward strand, were eliminated. The reference genome was then filtered to include only those SNPs with a minor allele frequency (MAF) greater than 0.005. The data were then phased using SHAPEIT (Delaneau et al., *Nat. Methods,* 10:5-6 (2013)) and imputed via IMPUTE2 (Howie et al., *PLoS Genet.,* 5:e1000529 (2009)). SNPs with an imputation dosage allele r2 of at least 0.3, and a MAF of at least 0.01, were used in the pooled analyses.

Genetic Ancestry and Population Stratification

Genetic data were used to assign ancestry groups (African, Caucasian, or Asian) for individuals using the STRUCTURE software (Pritchard et al., *Genetics,* 155:945-959 (2000)), and using the 1000 Genomes data as a reference. These estimates were done within cohort and platform (San Diego/550, San Diego/650, US/Omni 2.5, Rochester/Omni 1). Others (Novembre et al., *Nature,* 456:98-101 (2008)) have shown that it is necessary to perform pruning of the SNPs to be used for eigenvectors in order to avoid having sample eigenvectors that are determined by small clusters of SNPs at specific locations, such as the lactose intolerance gene, or polymorphic inversion regions. Therefore, the SNPs used for STRUCTURE and for eigenvectors were selected by LD pruning from an initial pool consisting of all autosomal SNPs with the following filters: SNPs with a minor allele frequency (MAF)<5% were excluded; influential SNPs were removed (according to the following chromosome regions: chromosome 8 [bp 1-12700000]; chromosome 2 [bp 129900001-136800000, 5700000-33500000]; chromosome 4 [bp 0900001-44900000]); correlation (r2) pruning was used to subset to uncorrelated SNPs. SNPs passing these selection criteria were input to STRUCTURE (Pritchard et al., *Genetics,* 155:945-959 (2000)) to make ancestry "triangle" plots that depict the admixture proportions of ancestry groups for each subject. Subjects were classified into major ancestry groups based on the largest estimated STRUCTURE ancestry proportion.

Eigenvectors were estimated within ancestry groups and platform strata for refined control of population stratification. For this step, SNPs with a MAF<0.01 were excluded, SNPs with a HWE p-value<0.001 were excluded, INDELS were removed, and pruning according to variance inflation factors was used. These data were then used with smartPCA to produce a set of eigenvectors using the normalization formulas of Price et al. (*Nature Genetics,* 38:904-909 (2006)) following the procedures of EIGENSTRAT. Tracy-Widom statistics were computed to include eigenvectors as potential for adjusting covariates if they had a p-value<0.05.

Selection of Covariates to Adjust for Potential Confounders

To remove the effects of potential confounders so that the cohorts could be combined, a screen for potential confounders relevant to each ancestry group and cohort was performed. The immune response trait measles-specific IFNγ ELISPOT, as well as the measles-specific secreted cytokines, were transformed by normal quantiles of the difference of the mean stimulated and mean unstimulated values.

Neutralizing antibody titer was transformed as the natural log of the PRMN mIU/mL value. Possible confounders were screened for their association with the trait using the following steps. Any categorical variable with a very large number of categories was binned using hierarchical clustering. This was achieved by using hierarchical clustering on the estimated regression coefficients for the different categories, binning categories with similar regression coefficients. All categorical variables were coded as dummy variables such that the most common category was used as baseline. Variables that were marginally associated with the trait with p-value<0.1 were then included in backwards selection with a p-value threshold of 0.1. This somewhat liberal threshold achieved the goal of controlling for potential confounding covariates. Residuals from the final "covariate models" were then used as the primary adjusted traits for GWAS analyses.

GWAS Pooled Analysis

The adjusted traits for IFNγ ELISPOT and neutralizing antibody were pooled over the three cohorts and genotype platforms to perform the pooled GWAS analysis. To pool the genotypes, the genotypes that were imputed separately within each platform were used. To analyze Caucasian and African-American ancestry together, a linear regression model that included a cohort indicator, ancestry indicator, dose of minor allele, and interaction of ancestry with dose of minor allele was used. This full model was compared with a reduced model that included a cohort indicator and ancestry indicator. The full and reduced models were used to create a likelihood ratio test for the effect of a SNP, allowing for the possible interaction of the SNP with ancestry, resulting in a test with two degrees of freedom (df). To test for the effect of a SNP within an ancestry group, a cohort indicator was only used as an adjusting factor, resulting in a test with one df for the SNP effect. The measles-specific secreted cytokines were only measured in the Rochester cohort, so the resulting test for SNP effects was based on a one df statistic. All reported p-values are two-sided. To control for multiple testing, the standard p-value<$5.0\times10^{-8}$ was used (Manolio, *New Engl. J. Med.,* 363:166-76 (2010); and Pe'er et al., *Genetic Epidemiology,* 32:381-5 (2008)) to determine genome-wide statistical significance. Statistical analyses were performed with the R 3.2.0 statistical software and PLINK (Purcell et al., *Am. J. Hum. Genet.,* 81:559-575 (2007)).

Analysis of mRNA-Seq Data for Differential Exon Usage

Evidence of differential exon usage in the CD46 and IFI44L genes was tested for using the method of Anders et al., implemented in the DEXSeq package (version 1.16.10) in the R programming language (version 3.2.3) (Anders et al., *Genome Res.,* 22:2008-17 (2012)). This method utilized generalized linear models (GLM) fitting per-gene negative binomial models. For the full model, main effects for the sample, exon, and an interaction between the exon and allele state/genotype (subjects' homozygous minor allele compared to heterozygous and homozygous major allele) were included. The likelihood estimate from the full model was compared to the likelihood from the model with the main effects to test the hypothesis for differential exon usage between the different genotypes/allele states. A significant test for a given exon provides evidence of differential exon usage (i.e., an alternative splicing event to produce different transcripts/isoforms). The per-exon estimates of the dispersion for the negative binomial GLMs were calculated using the Cox-Reid method (Anders et al., *Genome Res.,* 22:2008-17 (2012); Cox and Reid, *J. Royal Stat. Soc. Ser. B Methodol.,* 49:1-39 (1987); and McCarthy et al., *Nucleic Acids Res.,* 40:4288-97 (2012)) applied to all of the observed exons from the experiment based on the full model. To limit the risk of false discovery, the analyses of differential exon usage were limited to the CD46 (n=14 exons) and IFI44L (n=9 exons) genes. The method of Benjamini and Hochberg was used to control the false discovery rate, and the adjusted p-values were reported as q-values (Benjamini and Hochberg, *J. Royal Stat. Soc.* Series B, 57:289-300 (1995)). mRNA-Seq paired-end sequencing data on 28 subjects (selected based on the extremes of the distribution of the antibody response, 14 high and 14 low antibody responders) was used to test the hypothesis of differential exon usage (exon expression) between different genotypes of interest (for CD46 rs2724374 and for IFI44L rs1333973/rs273259).

Molecular Modeling

In order to evaluate the effect of differential splicing on the dynamics of the CD46 molecular structure, homology models (Roy et al., *Nature Protocols,* 5:725-38 (2010)) were generated of the extracellular domains (SCR1-4 and STP domains) for each isoform and analyzed each using Anisotropic Network Models (ANMs) (Atilgan et al., *Biophysical J.,* 80:505-15 (2001); Chennubhotla and Bahar, *PLoS Computational Biol.,* 3:1716-26 (2007); and Yang et al., *PNAS,* 106:12347-52 (2009)) using multiple templates. The crystal structure of MV-H and its interactions between with CD46 and MV-H were taken modeled from using the crystal structure PDB 3INB (Santiago et al., *Nature Struct. Mol. Biol.,* 17:124-9 (2010)) as a template wherein dimeric MV-H is bound symmetrically by the SCR1 and SCR2 domains of two CD46 molecules.

No full-length structure of CD46 exists, but partial structures of the extracellular domains have been solved. These cover the sequences encoded by the first six exons of the gene. Available experimental structures include the co-crystal structure between CD46 SCR1-4 and the adenovirus type 11 knob (3o8e (Persson et al., *PLoS Pathogens,* 6:e1001122 (2010)), and a co-crystal structure of CD46 SCR1-2 bound to the MV-H globular head domain dimer (3inb; Santiago et al., *Nature Struct. Mol. Biol.,* 17:124-9 (2010)). Computationally determined models have also been deposited in MODBASE (Pieper et al., *Nucl. Acids Res.,* 32:D217-22 (2004)). Homology models of the extracellular domains (SCR1-4 and STP domains) of ABC1, BC1, and C1 isoforms of CD46 (identical to ABC2, BC2, and C2, respectively) were generated using I-TASSER (Roy et al., *Nature Protocols,* 5:725-38 (2010)) and compared them to the MODBASE models and available crystal structures, in order to evaluate model quality and consistency.

In order to evaluate the effect of differential splicing on the dynamics of the CD46 structure, Anisotropic Network Models (ANMs) (Zimmermann et al., *BMC Bioinformatics,* 12:264 (2011); and Atilgan et al., *Biophys.* 1, 80:505-15 (2001)) were generated using a distance-dependent interaction strength (Yang et al., *PNAS,* 106:12347-52 (2009)). Models were evaluated using computed Mean Squared Fluctuations as a per-residue measure of mobility, commute time (Chennubhotla and Bahar, *PLoS Comput. Biol.,* 3:1716-26 (2007)) as a measure of efficiency with which information passes through the structure, and angle monitors to evaluate overall domain-domain orientations. The motions computed by ANM are theoretically local (small-scale), but often correlate strongly with large-scale functional motions. Thus, the functional magnitudes of ANM motions were not intrinsically defined. Therefore, each structure was deformed to 2 Å RMSD in each direction of a given mode as a consistent and realistic extent of motion.

The crystal structure of the MV-H head domain dimer and its interactions with CD46 were taken from PDB 3INB (Santiago et al., *Nature Struct. Mol. Biol.*, 17:124-9 (2010)), and its dynamics was modeled using ANM. Motions of bound CD46 molecules induced by these intrinsic motions of MV-H were inferred by rigidly tethering SCR1 and SCR2 to their interacting residues in the crystal structure. Diagram mModels of MV-F were produced by Gaussian smoothing of the molecular surface of 1G5G (Chen et al., *Structure*, 9:255-66 (2001))—the fusion protein of Newcastle disease virus/NDV which, like MV, is a member of the Paramyxoviridae family.

Results

Genome-Wide Analysis Results with Humoral Immunity

Figure 2A:
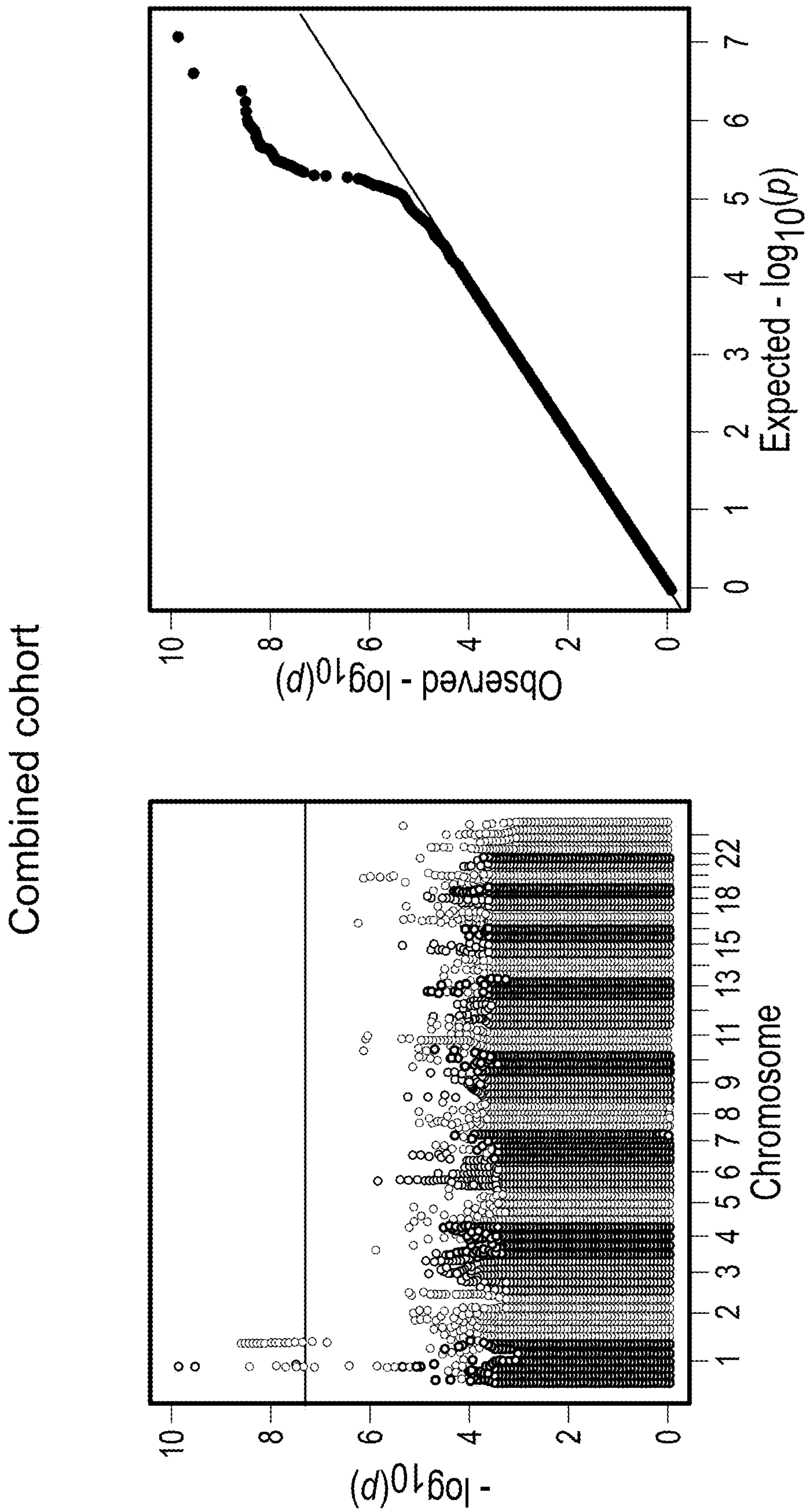
FIGS. 2A-2B. Manhattan and Q-Q plots summary of genome-wide association study associations between SNPs and measles-specific neutralizing antibody titers. (A) Manhattan (left panel) and Q-Q (right panel) plots for the combined cohort analysis (n=2872; reduced to 2818 after excluding subjects with neutralizing antibody data, that failed QC). (B) Manhattan (left panel) and Q-Q (right panel) plots for the subset analysis of subjects of Caucasian ancestry (n=2555; reduced to 2506 after excluding subjects with neutralizing antibody data, that failed QC).
Figure 2B:
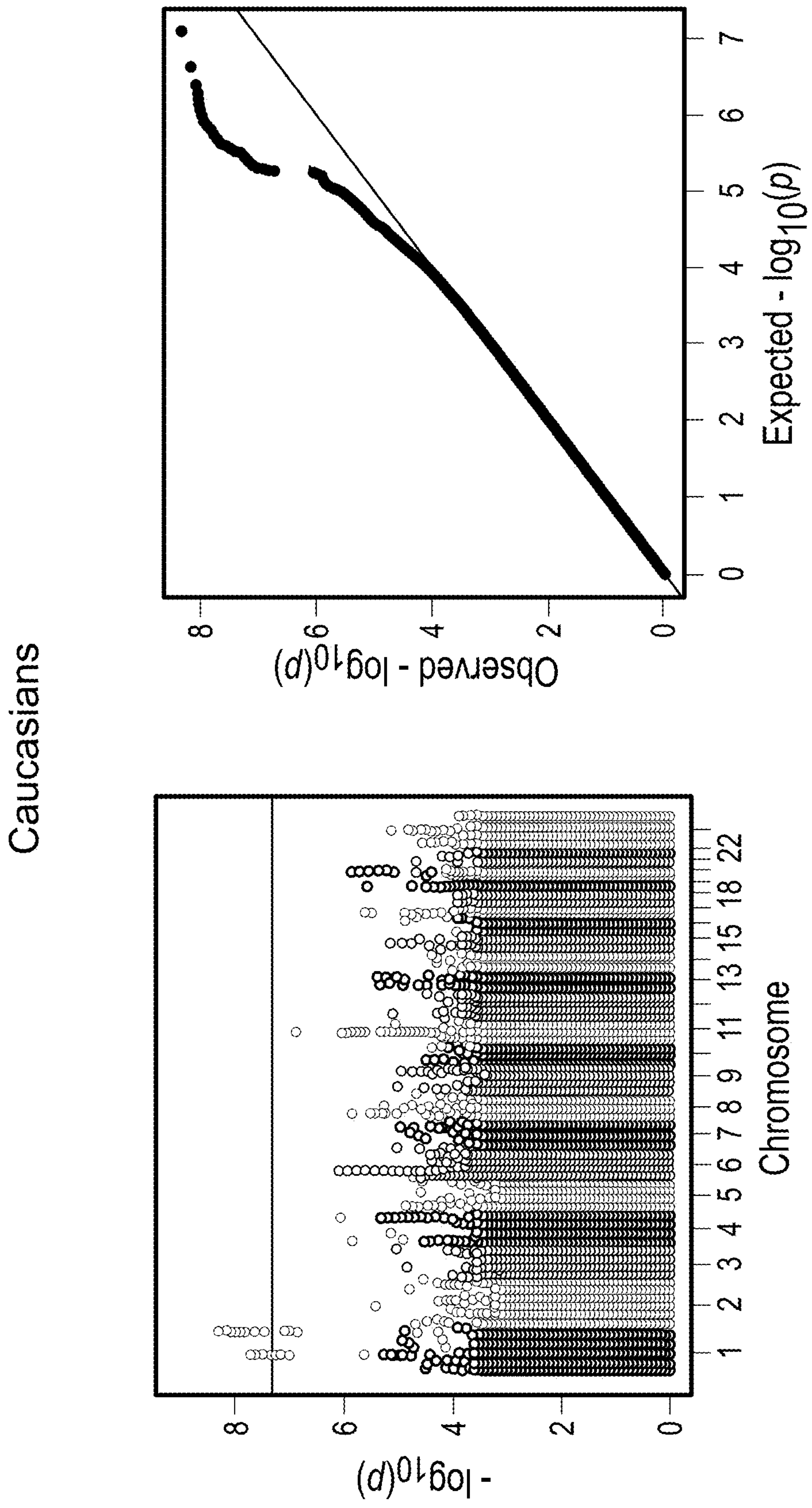

Genetic Regions Associated with Variations in Measles-Specific Antibody Response after Vaccination The demographic and immune characteristics of the study sample (n=2,872) are summarized in Table 1. Two independent gene regions on chromosome 1 associated with antibody response following measles vaccination were identified (FIGS. 1 and 2). As depicted on the locus zoom plot (FIG. 1A), the right region on chromosome 1 contained multiple SNPs (n=20) in/around the MV receptor-encoding CD46 gene and region (1q32, bp 207917499-208025926, NCBI Build 37/hg19). Analyzing associations between antibody response and SNPs in the two other MV receptors on chromosome 1, SLAM (SLAMF1) and nectin-4 (NECTIN4/PVRL4), did not result in significant findings. The left region (FIG. 1C) on chromosome 1 (1p31.1, bp 79082772-79110518) contained nine significant SNPs in/around the interferon-induced, protein 44-like gene IFI44L.

Figure 3:
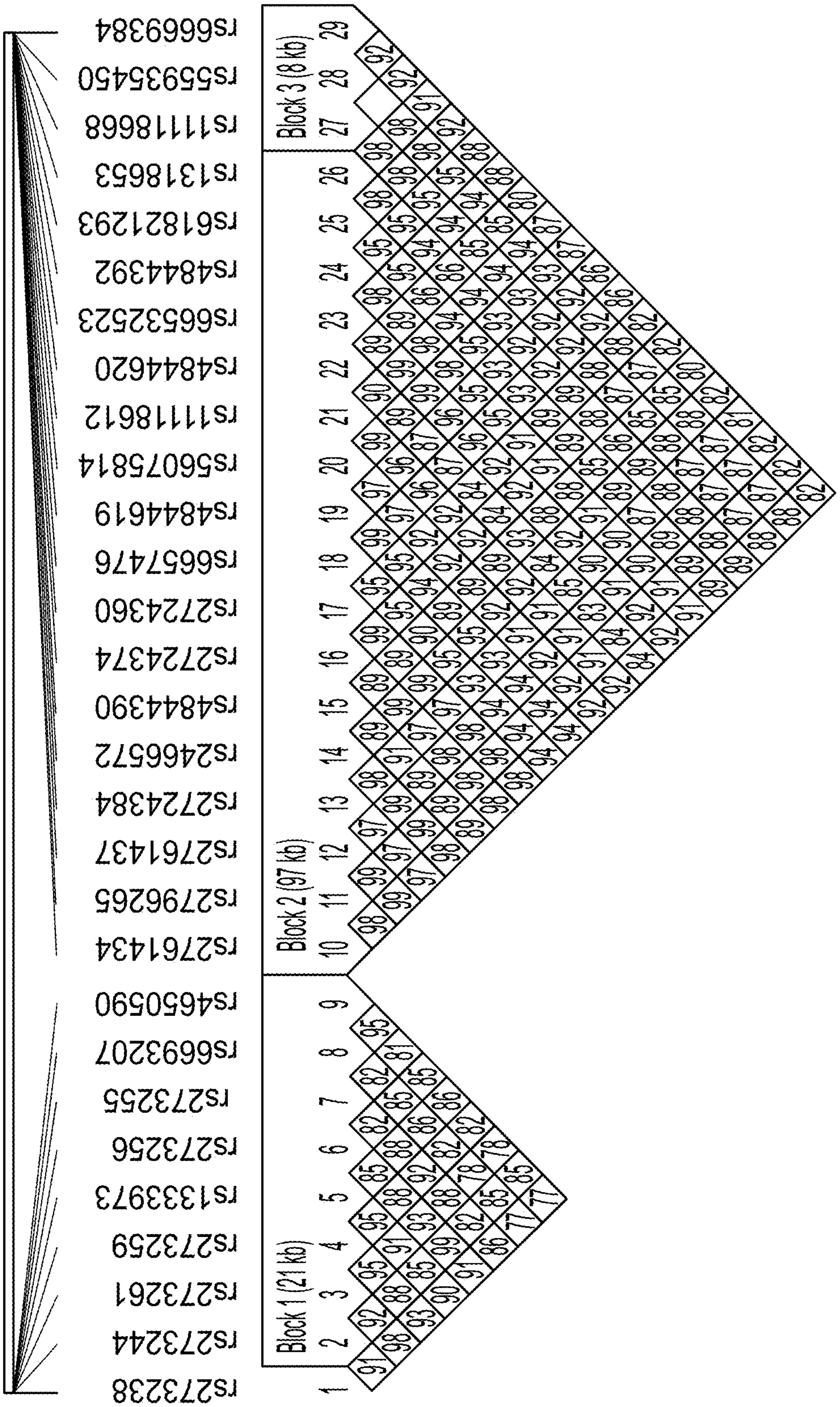
FIG. 3. Haplotype block structure of the significant IFI44L and CD46 SNPs associated with measles-specific antibody response (combined sample). The schematic representation and LD block structure of IFI44L (left) and CD46 (right) genetic regions are depicted (significantly associated SNPs only). The LD block structure was analyzed using Haploview software, version 4.2. The $r^2$ color scheme is: white ($r^2$=0), shades of grey ($0<r^2<1$), black ($r^2$=1). The numbers report the $r^2$ value multiplied by 100.

CD46 Region SNPs Associated with Variations in Measles-Specific Antibody Response after Vaccination The genetic association signal from the 1q32 region was linked to two blocks (97 kb and 8 kb) of 20 genetic variants in and around the CD46 gene (seven intronic CD46 SNPs, four SNPs in the uncharacterized LOC101929385 (currently Gene ID 100128537, C1orf132 chromosome 1 open reading frame 132), and nine intergenic SNPs, including the previously reported rs1318653 (Feenstra et al., *Nature Genetics*, 46:1274-82 (2014)), located between CD46 and CD34), which were in high linkage disequilibrium (LD) (FIG. 3). The most significant CD46 SNPs, rs2724384 and rs2724374 (in high LD, r2=97), lie in intron 1, and near the boundary of intron 8 (of the reference sequence ENST00000358170, RefSeq NM_002389), respectively. The minor alleles (G) of rs2724384 and rs2724374 were significantly associated (Table 2) with an allele dose-related decrease in measles-specific neutralizing antibody titers after vaccination (46-47% decrease in antibody titer in homozygous minor allele genotype subjects compared to homozygous major allele genotype subjects, Table 2, FIG. 1B). Due to the high LD (FIG. 3), all significant CD46 SNPs displayed similar effects. Most of the 1q32 associations remained genome-wide significant ($p<5.0\times10^{-8}$) in the subjects of Caucasian ancestry, where the most significant SNP was rs2724374 (p-value$=4.88\times10^{-9}$, Table 3).

TABLE 2

Genome-wide significant associations of SNPs with measles-specific neutralizing antibody titers after MMR vaccination (combined analysis, n = 2872[a]).

| SNP ID[b] | Gene/Location[c] | Major allele | Minor allele | MAF[d] | P-value[e] | Obs.0[f] |
|---|---|---|---|---|---|---|
| rs1333973 | IFI44L, intron | T | A | 0.32 | 1.41E−10 | 1289 |
| rs273259 | IFI44L, missense | A | G | 0.33 | 2.87E−10 | 1253 |
| rs2724384 | CD46, intron | A | G | 0.23 | 2.64E−09 | 1680 |
| rs2761437 | . | G | A | 0.23 | 3.14E−09 | 1671 |
| rs2724374 | CD46, intron | T | G | 0.23 | 3.16E−09 | 1666 |
| rs2796265 | . | T | C | 0.23 | 3.70E−09 | 1671 |
| rs4650590 | IFI44L, 3'UTR | A | G | 0.33 | 3.72E−09 | 1266 |
| rs11118612 | LOC101929385 | T | A | 0.23 | 4.06E−09 | 1685 |
| rs2761434 | . | G | A | 0.23 | 4.97E−09 | 1671 |
| rs4844392 | LOC101929385 | C | G | 0.23 | 5.26E−09 | 1688 |
| rs4844619 | CD46, intron | C | T | 0.23 | 5.40E−09 | 1685 |
| rs2466572 | CD46, intron | C | A | 0.23 | 6.33E−09 | 1668 |
| rs2724360 | CD46, intron | T | C | 0.23 | 6.51E−09 | 1664 |
| rs6657476 | CD46, intron | G | T | 0.23 | 6.51E−09 | 1687 |
| rs56075814 | . | T | C | 0.23 | 9.15E−09 | 1682 |
| rs6669384 | . | T | C | 0.22 | 1.06E−08 | 1711 |
| rs55935450 | . | T | A | 0.22 | 1.21E−08 | 1702 |
| rs6693207 | IFI44L, 3'UTR | G | A | 0.33 | 1.23E−08 | 1273 |
| rs273255 | IFI44L, intron | A | T | 0.32 | 1.24E−08 | 1311 |
| rs11118668 | . | C | T | 0.22 | 1.30E−08 | 1702 |
| rs66532523 | LOC101929385 | A | C | 0.23 | 1.45E−08 | 1683 |
| rs273261 | IFI44L, intron | G | A | 0.34 | 2.03E−08 | 1223 |
| rs4844620 | LOC101929385 | G | A | 0.21 | 2.18E−08 | 1762 |
| rs1318653 | . | T | C | 0.22 | 2.94E−08 | 1708 |
| rs273256 | IFI44, intron | A | C | 0.36 | 3.15E−08 | 1166 |
| rs273244 | IFI44L, intron | A | T | 0.36 | 3.30E−08 | 1162 |
| rs61821293 | . | T | G | 0.22 | 4.14E−08 | 1697 |
| rs273238 | . | G | A | 0.35 | 4.37E−08 | 1220 |
| rs4844390 | CD46, intron | A | G | 0.21 | 4.63E−08 | 1753 |

| SNP ID[b] | Obs.1[f] | Obs.2[f] | Median (IQR) 0[g] | Median (IQR) 1[g] | Median (IQR) 2[g] |
|---|---|---|---|---|---|
| rs1333973 | 1230 | 299 | 1010 (440, 1919) | 772 (363, 1491) | 625 (314, 1304) |
| rs273259 | 1250 | 315 | 1003 (438, 1879) | 777 (364, 1520) | 631 (326, 1304) |
| rs2724384 | 999 | 139 | 978 (429, 1882) | 710 (363, 1468) | 516 (272, 884) |
| rs2761437 | 1003 | 144 | 981 (431, 1881) | 710 (359, 1475) | 517 (283, 884) |
| rs2724374 | 1006 | 146 | 978 (430, 1881) | 717 (361, 1470) | 526 (277, 884) |

TABLE 2-continued

Genome-wide significant associations of SNPs with measles-specific neutralizing antibody titers after MMR vaccination (combined analysis, n = 2872[a]).

| | | | | | |
|---|---|---|---|---|---|
| rs2796265 | 1002 | 145 | 981 (431, 1881) | 710 (358, 1470) | 518 (286, 884) |
| rs4650590 | 1226 | 326 | 1022 (450, 1932) | 755 (361, 1470) | 650 (329, 1327) |
| rs11118612 | 991 | 142 | 978 (432, 1882) | 703 (347, 1435) | 545 (300, 972) |
| rs2761434 | 1002 | 145 | 981 (431, 1881) | 710 (358, 1463) | 518 (286, 884) |
| rs4844392 | 987 | 143 | 978 (432, 1882) | 707 (345, 1443) | 545 (301, 952) |
| rs4844619 | 993 | 140 | 973 (430, 1879) | 712 (354, 1462) | 539 (291, 891) |
| rs2466572 | 1005 | 145 | 978 (430, 1880) | 715 (361, 1473) | 533 (286, 884) |
| rs2724360 | 1009 | 145 | 980 (430, 1880) | 715 (360, 1473) | 533 (286, 884) |
| rs6657476 | 991 | 140 | 972 (430, 1878) | 710 (354, 1462) | 539 (291, 891) |
| rs56075814 | 993 | 143 | 976 (431, 1879) | 708 (347, 1450) | 545 (301, 952) |
| rs6669384 | 980 | 127 | 970 (431, 1884) | 709 (349, 1420) | 545 (296, 992) |
| rs55935450 | 981 | 135 | 978 (430, 1885) | 703 (348, 1417) | 552 (301, 1013) |
| rs6693207 | 1223 | 322 | 1023 (455, 1932) | 753 (354, 1479) | 650 (340, 1316) |
| rs273255 | 1222 | 285 | 1005 (439, 1873) | 771 (362, 1504) | 637 (330, 1299) |
| rs11118668 | 981 | 135 | 978 (430, 1885) | 703 (348, 1417) | 552 (301, 1013) |
| rs66532523 | 992 | 143 | 974 (432, 1875) | 709 (347, 1455) | 545 (301, 952) |
| rs273261 | 1251 | 344 | 997 (438, 1857) | 774 (363, 1522) | 662 (335, 1366) |
| rs4844620 | 937 | 119 | 971 (430, 1876) | 701 (347, 1417) | 495 (280, 884) |
| rs1318653 | 976 | 134 | 972 (430, 1882) | 705 (347, 1417) | 565 (303, 1023) |
| rs273256 | 1277 | 375 | 1002 (445, 1898) | 774 (362, 1520) | 691 (349, 1398) |
| rs273244 | 1280 | 376 | 1004 (445, 1898) | 772 (362, 1520) | 694 (349, 1417) |
| rs61821293 | 984 | 137 | 970 (430, 1879) | 710 (347, 1426) | 561 (302, 992) |
| rs273238 | 1249 | 349 | 996 (438, 1845) | 779 (363, 1528) | 658 (338, 1359) |
| rs4844390 | 940 | 125 | 974 (427, 1883) | 702 (357, 1419) | 495 (274, 880) |

[a]Reduced to 2818 after excluding subjects with immune outcome data that failed QC

[b]SNP identification number

[c]Gene/genetic region and SNP location relative to the gene

[d]Minor allele frequency

[e]P-values

[f]Number of subjects with homozygous major allele genotype (0), heterozygous (1) and homozygous minor allele genotype (2)

[g]Median neutralizing antibody titer (in miU/mL, with 25% and 75% inter-quartile range/IQR) for subjects with homozygous major allele genotype (0), heterozygous (1) and homozygous minor allele genotype (2)

TABLE 3

Top significant associations of SNPs with measles-specific neutralizing antibody titers after MMR vaccination (Caucasians, n = 2555[a])

| SNP ID[b] | Gene/Location[c] | Major allele | Minor allele | MAF[d] | P-value[e] | Obs.0[f] |
|---|---|---|---|---|---|---|
| rs2724374 | CD46, intron | T | G | 0.23 | 4.88E−09 | 1462 |
| rs2761437 | | G | A | 0.23 | 6.98E−09 | 1467 |
| rs2796265 | | T | C | 0.23 | 8.25E−09 | 1467 |
| rs2466572 | CD46, intron | C | A | 0.23 | 9.49E−09 | 1464 |
| rs4844619 | CD46, intron | C | T | 0.23 | 1.05E−08 | 1468 |
| rs6657476 | CD46, intron | G | T | 0.23 | 1.06E−08 | 1468 |
| rs2724360 | CD46, intron | T | C | 0.23 | 1.18E−08 | 1461 |
| rs2761434 | | G | A | 0.23 | 1.19E−08 | 1467 |
| rs2724384 | CD46, intron | A | G | 0.23 | 1.27E−08 | 1466 |
| rs4844620 | LOC101929385 | G | A | 0.23 | 1.64E−08 | 1490 |
| rs4844392 | LOC101929385 | C | G | 0.23 | 1.69E−08 | 1461 |
| rs11118612 | LOC101929385 | T | A | 0.23 | 1.98E−08 | 1461 |
| rs1333973 | IFI44L, intron | T | A | 0.33 | 2.10E−08 | 1122 |
| rs66532523 | LOC101929385 | A | C | 0.23 | 2.27E−08 | 1461 |
| rs56075814 | | T | C | 0.23 | 2.34E−08 | 1460 |
| rs273259 | IFI44L, missense | A | G | 0.33 | 2.62E−08 | 1118 |
| rs273261 | IFI44L, intron | G | A | 0.34 | 3.41E−08 | 1110 |
| rs4844390 | CD46, intron | A | G | 0.23 | 3.48E−08 | 1478 |
| rs6669384 | | T | C | 0.23 | 3.75E−08 | 1484 |
| rs273256 | IFI44L, intron | A | C | 0.35 | 5.10E−08 | 1052 |
| rs273244 | IFI44L, intron | A | T | 0.35 | 6.35E−08 | 1050 |
| rs4650590 | IFI44L, 3'UTR | A | G | 0.35 | 6.58E−08 | 1065 |
| rs273238 | | G | A | 0.34 | 6.91E−08 | 1108 |
| rs55935450 | | T | A | 0.23 | 6.93E−08 | 1477 |
| rs11118668 | | C | T | 0.23 | 7.38E−08 | 1477 |
| rs61821293 | | T | G | 0.23 | 8.51E−08 | 1475 |
| rs6693207 | IFI44L, downstream | G | A | 0.35 | 9.28E−08 | 1069 |
| rs273255 | IFI44L, intron | A | T | 0.32 | 1.01E−07 | 1149 |
| rs1318653 | | T | C | 0.23 | 1.04E−07 | 1480 |

TABLE 3-continued

Top significant associations of SNPs with measles-specific neutralizing antibody titers after MMR vaccination (Caucasians, n = 2555[a])

| SNP ID[b] | Obs.1[f] | Obs.2[f] | Antibody titer Median (IQR) 0[g] | Antibody titer Median (IQR) 1[g] | Antibody titer Median (IQR) 2[g] |
|---|---|---|---|---|---|
| rs2724374 | 915 | 129 | 924 (414, 1799) | 703 (352, 1418) | 516 (274, 843) |
| rs2761437 | 912 | 127 | 924 (414, 1797) | 702 (349, 1422) | 515 (280, 825) |
| rs2796265 | 911 | 128 | 924 (414, 1797) | 702 (349, 1420) | 515 (283, 847) |
| rs2466572 | 914 | 128 | 924 (414, 1798) | 703 (350, 1418) | 517 (283, 847) |
| rs4844619 | 914 | 124 | 916 (414, 1794) | 705 (348, 1420) | 526 (283, 864) |
| rs6657476 | 914 | 124 | 916 (414, 1794) | 705 (348, 1420) | 526 (283, 864) |
| rs2724360 | 917 | 128 | 924 (414, 1798) | 703 (349, 1418) | 517 (283, 847) |
| rs2761434 | 910 | 129 | 924 (414, 1797) | 702 (349, 1418) | 516 (286, 858) |
| rs2724384 | 914 | 126 | 924 (414, 1798) | 702 (354, 1418) | 506 (277, 854) |
| rs4844620 | 899 | 117 | 913 (416, 1772) | 701 (345, 1405) | 495 (286, 884) |
| rs4844392 | 917 | 128 | 919 (416, 1793) | 702 (344, 1418) | 539 (291, 883) |
| rs11118612 | 918 | 127 | 918 (416, 1793) | 702 (346, 1417) | 533 (290, 884) |
| rs1333973 | 1106 | 278 | 942 (422, 1768) | 759 (361, 1448) | 616 (306, 1283) |
| rs66532523 | 917 | 128 | 918 (416, 1793) | 702 (345, 1417) | 539 (291, 883) |
| rs56075814 | 918 | 128 | 917 (416, 1794) | 703 (346, 1417) | 539 (291, 883) |
| rs273259 | 1104 | 284 | 942 (424, 1765) | 757 (356, 1455) | 628 (319, 1284) |
| rs273261 | 1106 | 290 | 950 (428, 1768) | 754 (355, 1441) | 631 (323, 1287) |
| rs4844390 | 907 | 121 | 919 (414, 1795) | 702 (352, 1417) | 495 (274, 858) |
| rs6669384 | 909 | 113 | 916 (414, 1797) | 703 (349, 1410) | 545 (293, 884) |
| rs273256 | 1134 | 320 | 958 (435, 1806) | 743 (347, 1448) | 646 (329, 1301) |
| rs273244 | 1136 | 320 | 964 (434, 1807) | 740 (348, 1438) | 646 (329, 1311) |
| rs4650590 | 1131 | 310 | 945 (432, 1808) | 739 (352, 1440) | 646 (329, 1316) |
| rs273238 | 1105 | 293 | 950 (427, 1766) | 758 (355, 1436) | 630 (327, 1299) |
| rs55935450 | 910 | 119 | 916 (414, 1793) | 700 (347, 1407) | 545 (296, 898) |
| rs11118668 | 910 | 119 | 916 (414, 1793) | 700 (347, 1407) | 545 (296, 898) |
| rs61821293 | 910 | 121 | 911 (414, 1790) | 702 (345, 1415) | 561 (299, 884) |
| rs6693207 | 1131 | 306 | 956 (434, 1807) | 740 (346, 1447) | 643 (337, 1306) |
| rs273255 | 1095 | 262 | 945 (426, 1769) | 735 (348, 1417) | 634 (328, 1287) |
| rs1318653 | 907 | 119 | 909 (414, 1776) | 702 (345, 1414) | 561 (301, 898) |

[a]Reduced to 2506 after excluding subjects with immune outcome data that failed QC
[b]SNP identification number
[c]Gene/genetic region and SNP location relative to the gene
[d]Minor allele frequency
[e]P-values
[f]Number of subjects with homozygous major allele genotype (0), heterozygous (1) and homozygous minor allele genotype (2)
[g]Median neutralizing antibody titer (in miU/mL, with 25% and 75% inter-quartile range/IQR) for subjects with homozygous major allele genotype (0), heterozygous (1) and homozygous minor allele genotype (2)

IFI44L Region SNPs Associated with Variations in Measles-Specific Antibody Response after Vaccination The 1p31.1 region signal was linked to a 21-kb block of 8 IFI44L SNPs and one intergenic SNP, in high LD (FIG. 3). The two most significant IFI44L SNPs, rs1333973 and rs273259 (Table 2) were located in IFI44L intron 2 (boundary) and IFI44L exon 2, respectively. The missense SNP rs273259 (His73Arg, Ensembl transcript ENST00000370751), as well as the other significant SNPs, demonstrated an allele dose-related decrease in measles-specific neutralizing antibody titers (Table 2, FIG. 1D). Three of the nine SNPs remained genome-wide significant ($p<5.0\times10^{-8}$) in the subjects of Caucasian ancestry (Table 3).

To determine if there were multiple SNPs in each of the CD46 and IFI44L regions associated with the neutralizing antibody, with the effects of the SNPs adjusted for each other, elastic net was used to select SNPs. An advantage of elastic net is that it can select highly correlated SNPs, although it cannot give p-values for selected SNPs. Hence, after selection, the selected SNPs were evaluated in linear regression models. This resulted in the selection of two SNPs in the CD46 region and three SNPs in the IFI44L region, based on the Caucasian subjects. For the CD46 region, rs2724374 was found to be the most significant and the primary driving SNP ($p=4.3\times10^{-8}$), with rs11806810 having much less association (p=0.02) when the effects of the SNPs were adjusted for each other. For the IFI44L region, the SNPs rs12026737, rs1333973, and rs273259 were selected. However, rs273259 and rs1333973 were highly correlated ($r^2=0.99$), making it difficult to disentangle their effects and fit both in a regression model. When choosing rs1333973 (top significant SNP) over rs273259, rs1333973 ($p=2\times10^{-8}$) and rs12026737 ($p=6.0\times10^{-4}$) were found to have strong statistical associations, with effects adjusted for each other. Furthermore, the CD46 and IFI44L regions have associations that are independent of each other (since when the aforementioned SNPs were modeled together, the results were not significantly different from what was obtained when the regions were modeled separately).

Genome-Wide Analysis Results with Measles Vaccine Cellular Immunity

Figure 4:
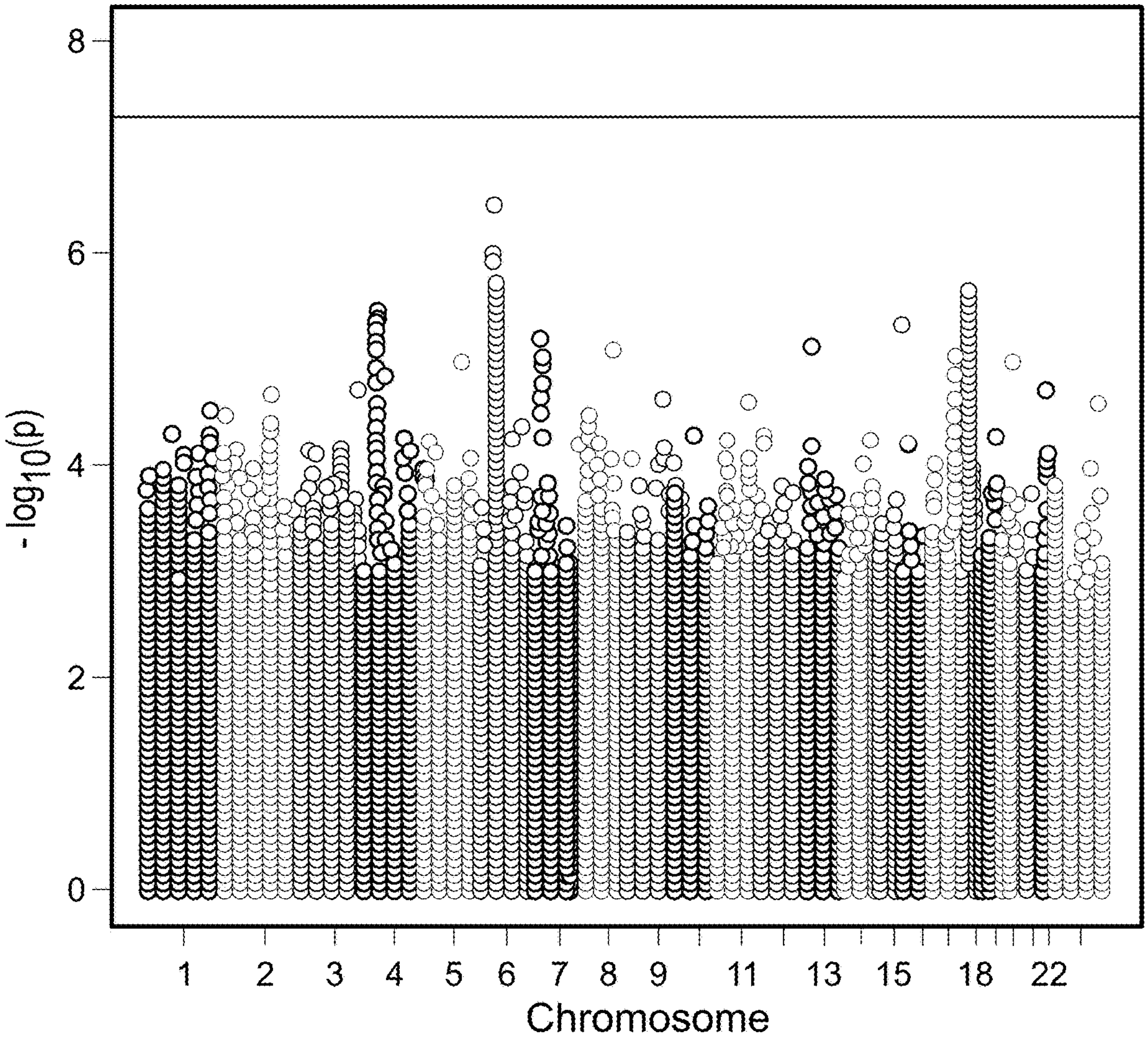
FIG. 4. Manhattan plot summary of genome-wide association study associations between SNPs and measles-specific IFNγ ELISPOT response in the combined cohort (n=2872; reduced to 2618 after excluding subjects with immune outcome data that failed QC).

The GWAS analyses did not reveal significant SNP associations with cellular immunity after vaccination, as measured by MV-specific IFNγ ELISPOT (Table 4, FIG. 4). Analyses of all chromosome 1 SNPs with MV-specific secreted cytokines in 625 Caucasian subjects (for whom cytokine data was available) demonstrated suggestive associations between CD46 SNPs (including rs2724374 and rs2724384) and the secretion of IFNγ; however, an allele-dose-dependency of IFNγ secretion was not noted (Table 5).

TABLE 4

Top 20 genome-wide associations of SNPs with measles-specific IFNγ ELISPOT response after MMR vaccination (Combined analysis, n = 2872[a])

| SNP ID[b] | Chr. | Gene[c] | Major allele | Minor allele | MAF[d] | P-value[e] | Obs.0[f] | Obs.1[f] | Obs.2[f] | IFNg ELISOT Median (IQR) 0[g] | IFNg ELISOT Median (IQR) 1[g] | IFNg ELISOT Median (IQR) 2[g] |
|---|---|---|---|---|---|---|---|---|---|---|---|---|
| rs140973961 | 6 | HLA-DRB5 | G | C | 0.34 | 1.05E−06 | 1138 | 1202 | 278 | 13 (6, 31) | 15 (6, 33) | 19 (8, 40) |
| rs115793823 | 6 | . | T | C | 0.24 | 1.25E−06 | 1479 | 1022 | 117 | 16 (7, 36) | 14 (6, 30) | 12 (5, 25) |
| rs115742047 | 6 | . | A | G | 0.26 | 2.18E−06 | 1422 | 1023 | 173 | 16 (7, 36) | 14 (6, 30) | 11 (5, 25) |
| rs116117104 | 6 | . | T | C | 0.26 | 2.62E−06 | 1412 | 1035 | 171 | 16 (7, 36) | 14 (6, 30) | 11 (5, 24) |
| rs114317125 | 6 | . | C | T | 0.26 | 2.63E−06 | 1412 | 1035 | 171 | 16 (7, 36) | 14 (6, 30) | 11 (5, 24) |
| rs116663036 | 6 | . | G | A | 0.26 | 2.63E−06 | 1412 | 1036 | 170 | 16 (7, 36) | 14 (6, 30) | 11 (5, 25) |
| rs182191708 | 6 | HLA-DRB5 | A | C | 0.30 | 2.94E−06 | 1253 | 1154 | 211 | 16 (7, 35) | 14 (6, 32) | 12 (5, 31) |
| rs114027708 | 6 | . | A | G | 0.23 | 2.98E−06 | 1546 | 939 | 133 | 16 (7, 35) | 13 (5, 30) | 13 (6, 26) |
| rs114854965 | 6 | . | C | T | 0.27 | 3.00E−06 | 1395 | 1051 | 172 | 16 (7, 37) | 14 (6, 30) | 11 (5, 24) |
| rs116230731 | 6 | . | C | T | 0.26 | 3.22E−06 | 1404 | 1041 | 173 | 16 (7, 36) | 14 (6, 30) | 11 (5, 24) |
| rs115383757 | 6 | . | T | A | 0.26 | 3.22E−06 | 1404 | 1041 | 173 | 16 (7, 36) | 14 (6, 30) | 11 (5, 24) |
| rs114274063 | 6 | . | T | G | 0.27 | 3.25E−06 | 1400 | 1047 | 171 | 16 (7, 37) | 14 (6, 30) | 11 (5, 24) |
| rs115052056 | 6 | . | T | A | 0.27 | 3.25E−06 | 1400 | 1047 | 171 | 16 (7, 37) | 14 (6, 30) | 11 (5, 24) |
| rs115613143 | 6 | . | C | T | 0.26 | 3.26E−06 | 1435 | 1021 | 162 | 16 (7, 36) | 14 (6, 30) | 12 (5, 26) |
| rs114634027 | 6 | . | A | G | 0.27 | 3.30E−06 | 1400 | 1047 | 171 | 16 (7, 37) | 14 (6, 30) | 11 (5, 24) |
| rs114250489 | 6 | . | G | A | 0.25 | 3.43E−06 | 1448 | 1045 | 125 | 16 (7, 36) | 14 (6, 30) | 12 (5, 25) |
| rs114759127 | 6 | . | T | A | 0.26 | 3.43E−06 | 1430 | 1025 | 163 | 16 (7, 36) | 14 (6, 30) | 11 (5, 24) |
| rs115751649 | 6 | . | T | C | 0.26 | 3.44E−06 | 1405 | 1040 | 173 | 16 (7, 36) | 14 (6, 30) | 11 (5, 25) |
| rs114332144 | 6 | . | C | T | 0.27 | 3.45E−06 | 1401 | 1045 | 172 | 16 (7, 37) | 14 (6, 30) | 11 (5, 25) |
| rs115712303 | 6 | . | C | G | 0.27 | 3.45E−06 | 1391 | 1053 | 174 | 16 (7, 37) | 14 (6, 30) | 11 (5, 25) |

[a]Reduced to 2618 after excluding subjects with immune outcome data that failed QC

[b]SNP identification number

[c]Gene/genetic region

[d]Minor allele frequency

[e]P-values

[f]Number of subjects with homozygous major allele genotype (0), heterozygous (1), and homozygous minor allele genotype (2)

[g]Median measles virus-specific ELISPOT response (IFNγ-positive spot-forming units/SFUs per 2 x $10^5$ cells, with 25% and 75% inter-quartile range/IQR) for subjects with homozygous major allele genotype (0), heterozygous (1) and homozygous minor allele genotype (2)

TABLE 5

Associations between chromosome 1 SNPs and measles virus-specific secreted IFNα (Caucasians, n = 625 subjects with available measles virus-specific cytokine data)

| SNP ID[a] | Gene/Location[b] | Major allele | Minor allele | MAF[c] | P-value[d] | Obs.0[e] |
|---|---|---|---|---|---|---|
| rs2724374 | CD46, intron | T | G | 0.23 | 0.0003 | 365 |
| rs2761437 | . | G | A | 0.23 | 0.0001 | 367 |
| rs2796265 | . | T | C | 0.23 | 0.0002 | 367 |
| rs2466572 | CD46, intron | C | A | 0.23 | 0.0003 | 366 |
| rs4844619 | CD46, intron | C | T | 0.23 | 0.0005 | 368 |
| rs6657476 | CD46, intron | G | T | 0.23 | 0.0005 | 368 |
| rs2724360 | CD46, intron | T | C | 0.23 | 0.0003 | 366 |
| rs2761434 | . | G | A | 0.23 | 0.0002 | 367 |
| rs2724384 | CD46, intron | A | G | 0.23 | 0.0003 | 367 |
| rs4844620 | LOC101929385 | G | A | 0.22 | 0.0004 | 374 |
| rs4844392 | LOC101929385 | C | G | 0.23 | 0.0003 | 369 |
| rs11118612 | LOC101929385 | T | A | 0.23 | 0.0003 | 367 |
| rs1333973 | IFI44L, intron | T | A | 0.33 | 0.4369 | 286 |
| rs66532523 | LOC101929385 | A | C | 0.23 | 0.0003 | 369 |
| rs56075814 | . | T | C | 0.23 | 0.0003 | 367 |
| rs273259 | IFI44L, missense | A | G | 0.33 | 0.4446 | 285 |
| rs273261 | IFI44L, intron | G | A | 0.33 | 0.4955 | 285 |
| rs4844390 | CD46, intron | A | G | 0.22 | 0.0002 | 369 |
| rs6669384 | . | T | C | 0.22 | 0.0016 | 371 |
| rs273256 | IFI44L, intron | A | C | 0.35 | 0.3759 | 269 |
| rs273244 | IFI44L, intron | A | T | 0.35 | 0.4476 | 267 |
| rs4650590 | IFI44L, 3'UTR | A | G | 0.35 | 0.2434 | 274 |
| rs273238 | . | G | A | 0.33 | 0.5265 | 284 |
| rs55935450 | . | T | A | 0.22 | 0.0007 | 373 |
| rs11118668 | . | C | T | 0.22 | 0.0007 | 373 |
| rs61821293 | . | T | G | 0.22 | 0.0005 | 372 |
| rs6693207 | IFI44L, downstream | G | A | 0.35 | 0.2152 | 276 |
| rs273255 | IFI44L, intron | A | T | 0.31 | 0.4163 | 300 |
| rs1318653 | . | T | C | 0.22 | 0.0012 | 373 |

TABLE 5-continued

Associations between chromosome 1 SNPs and measles virus-specific secreted IFNα (Caucasians, n = 625 subjects with available measles virus-specific cytokine data)

| SNP ID[a] | Obs.1[e] | Obs.2[e] | Median in pg/mL, IQR 0[f] | Median in pg/mL, IQR 1[f] | Median in pg/mL, IQR 2[f] |
|---|---|---|---|---|---|
| rs2724374 | 232 | 27 | 508 (251, 915) | 657 (329, 1169) | 575 (299, 1181) |
| rs2761437 | 230 | 27 | 508 (247, 914) | 656 (327, 1178) | 749 (370, 1181) |
| rs2796265 | 229 | 28 | 508 (247, 914) | 660 (330, 1183) | 662 (319, 1140) |
| rs2466572 | 231 | 27 | 510 (251, 914) | 660 (328, 1174) | 575 (299, 1181) |
| rs4844619 | 229 | 27 | 510 (252, 919) | 660 (326, 1164) | 575 (299, 1181) |
| rs6657476 | 229 | 27 | 510 (252, 919) | 660 (326, 1164) | 575 (299, 1181) |
| rs2724360 | 231 | 27 | 510 (251, 914) | 660 (328, 1174) | 575 (299, 1181) |
| rs2761434 | 229 | 28 | 508 (247, 914) | 660 (330, 1183) | 662 (319, 1140) |
| rs2724384 | 230 | 27 | 508 (252, 914) | 661 (327, 1178) | 575 (299, 1181) |
| rs4844620 | 228 | 22 | 515 (253, 926) | 656 (322, 1185) | 662 (296, 1221) |
| rs4844392 | 227 | 28 | 508 (243, 915) | 660 (328, 1152) | 662 (319, 1278) |
| rs11118612 | 229 | 28 | 511 (252, 922) | 652 (323, 1139) | 662 (319, 1278) |
| rs1333973 | 267 | 71 | 579 (256, 1013) | 568 (281, 1020) | 550 (320, 1110) |
| rs66532523 | 227 | 28 | 508 (243, 915) | 660 (328, 1152) | 662 (319, 1278) |
| rs56075814 | 229 | 28 | 511 (252, 922) | 652 (323, 1139) | 662 (319, 1278) |
| rs273259 | 266 | 73 | 580 (255, 1019) | 558 (280, 1013) | 576 (324, 1099) |
| rs273261 | 264 | 75 | 580 (255, 1019) | 558 (279, 1018) | 576 (335, 1072) |
| rs4844390 | 230 | 25 | 511 (252, 913) | 661 (327, 1187) | 575 (260, 1100) |
| rs6669384 | 234 | 19 | 523 (256, 957) | 645 (320, 1138) | 575 (331, 1181) |
| rs273256 | 268 | 87 | 578 (236, 996) | 558 (280, 1042) | 576 (335, 1041) |
| rs273244 | 271 | 86 | 580 (255, 996) | 550 (278, 1042) | 575 (329, 1023) |
| rs4650590 | 266 | 84 | 572 (241, 989) | 569 (287, 1042) | 575 (315, 1104) |
| rs273238 | 266 | 74 | 582 (257, 1025) | 558 (278, 1021) | 563 (329, 1043) |
| rs55935450 | 227 | 24 | 518 (251, 952) | 652 (325, 1152) | 662 (251, 1140) |
| rs11118668 | 227 | 24 | 518 (251, 952) | 652 (325, 1152) | 662 (251, 1140) |
| rs61821293 | 228 | 24 | 512 (249, 936) | 656 (329, 1169) | 662 (251, 1140) |
| rs6693207 | 263 | 85 | 572 (255, 986) | 569 (280, 1042) | 576 (324, 1099) |
| rs273255 | 258 | 66 | 574 (254, 996) | 569 (287, 1038) | 563 (318, 1100) |
| rs1318653 | 227 | 24 | 512 (251, 952) | 652 (328, 1152) | 662 (251, 1140) |

[a]SNP identification number

[b]Gene/genetic region and SNP location relative to the gene

[c]Minor allele frequency

[d]P-values

[e]Number of subjects with homozygous major allele genotype (0), heterozygous (1), and homozygous minor allele genotype (2)

[f]Median cytokine level (in pg/mL, with 25% and 75% inter-quartile range/IQR) for subjects with homozygous major allele genotype (0), heterozygous (1) and homozygous minor allele genotype (2)

Analysis of Differential Usage of Exons Using mRNA-Seq Data

Figure 5A:
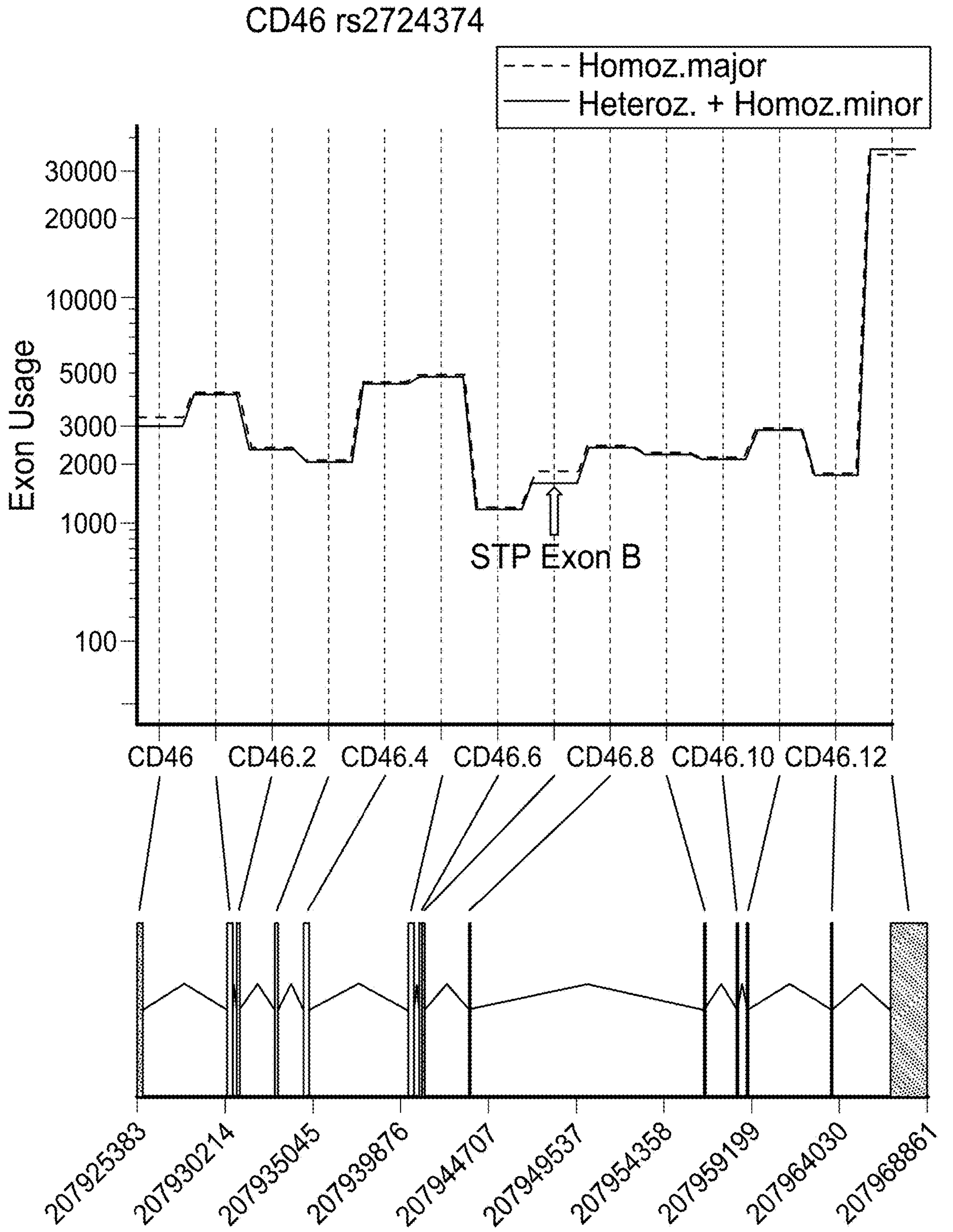
FIGS. 5A-5C. Differential exon/isoform CD46 and IFI44L usage. (A) Estimated exon usage in the CD46 gene comparing individuals with at least one minor allele (G for rs2724374, i.e., all the heterozygous subjects plus the one homozygous minor allele subject combined, total n=9) (blue) to individuals that are homozygous major (T for rs2724374) allele, n=19 (red). Even with a relatively small number of subjects possessing the minor allele genotype, differential exon usage with a highly significant p-value was observed for the STP exon B (genomic ID 207941124-207941168) ($p=2.96\times10^{-7}$). (B) RT-PCR analysis of common CD46 isoforms was performed in PBMCs of rs2724374 homozygous major allele genotype individuals (n=10) compared to homozygous minor allele genotype individuals (n=10) and heterozygous individuals (n=10). The presented figure is representative of the patterns observed in all 30 subjects (10 subjects per genotype group) with the experiment replicated twice. (C) Estimated exon usage in IFI44L rs1333973/rs273259 homozygous minor allele genotype subjects (A for rs1333973, n=5, blue) vs. homozygous major allele subjects (T for rs1333973, n=11, red). The results demonstrate significant per-exon estimates for several IFI44L exons, the most significant being exon 2 (genomic ID 79093591-79094078) ($q=2.37\times10^{-150}$).
Figure 5B:
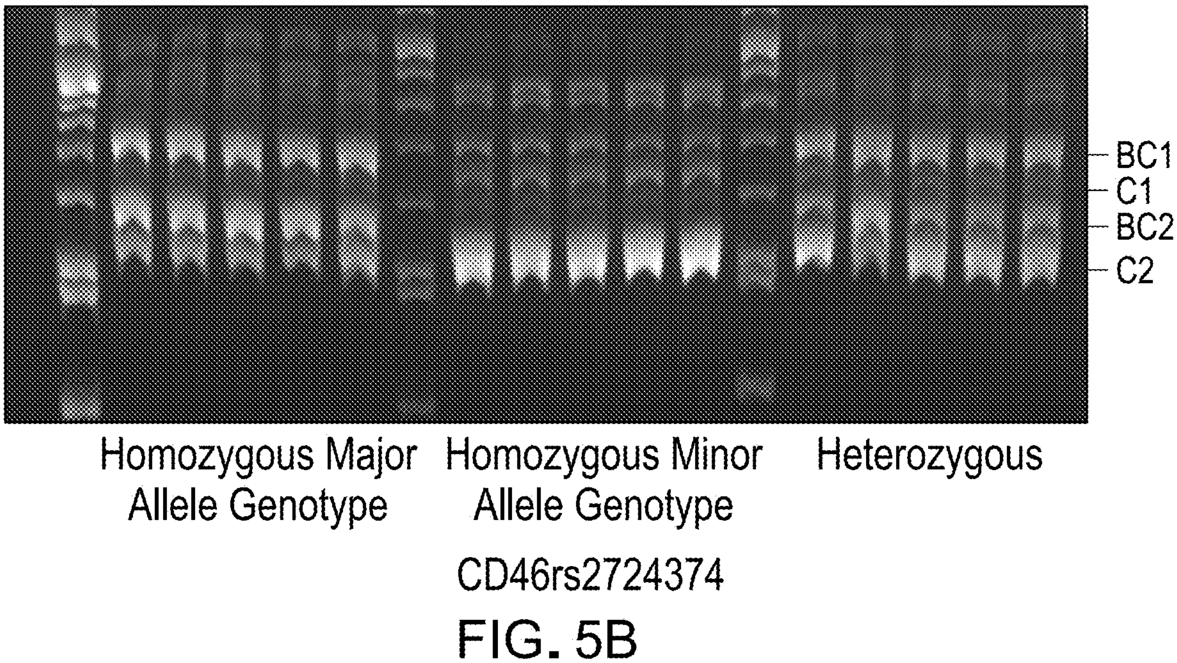
Figure 5C:
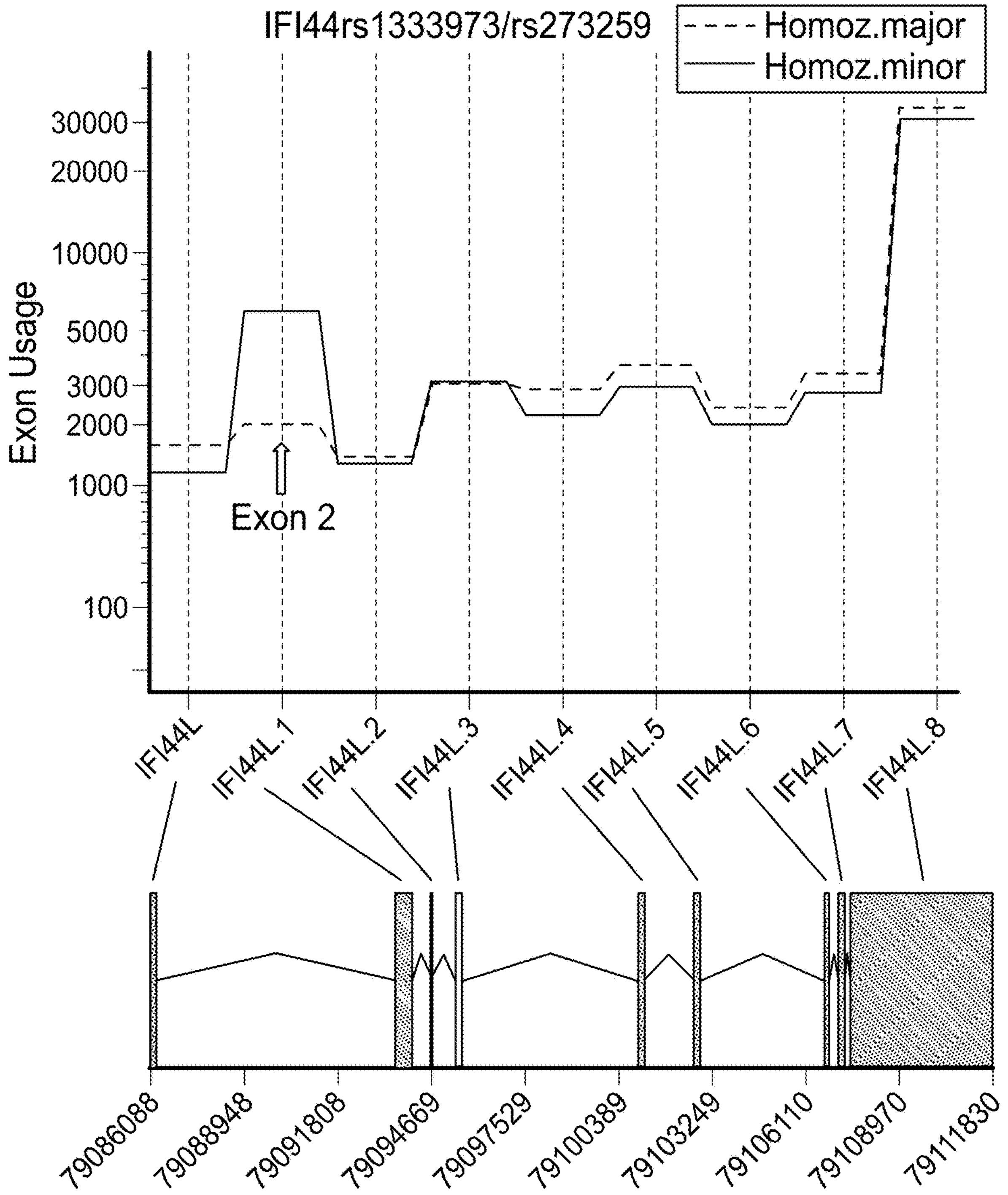

In the CD46 analyses, a highly significant per-exon estimate ($q=2.96\times10^{-7}$) with lower exon B (in the CD46 STP region) expression (exon skipping) was observed in subjects with rs2724374 minor G allele (FIG. 5A). These results were further confirmed by RT-PCR analysis of common CD46 isoforms in PBMCs. In this analysis, the predominant "lower band" CD46 isoform phenotype (C2, associated with exon B skipping) was clearly more pronounced in the homozygous minor G allele genotype subjects (FIG. 5B). Differential exon usage based on IFI44L rs1333973/rs273259 genotypes also was observed (FIG. 5C).

Simulation of the Structural Differences Between CD46 Isoforms (with or without the STP Exon B)

Figure 6:
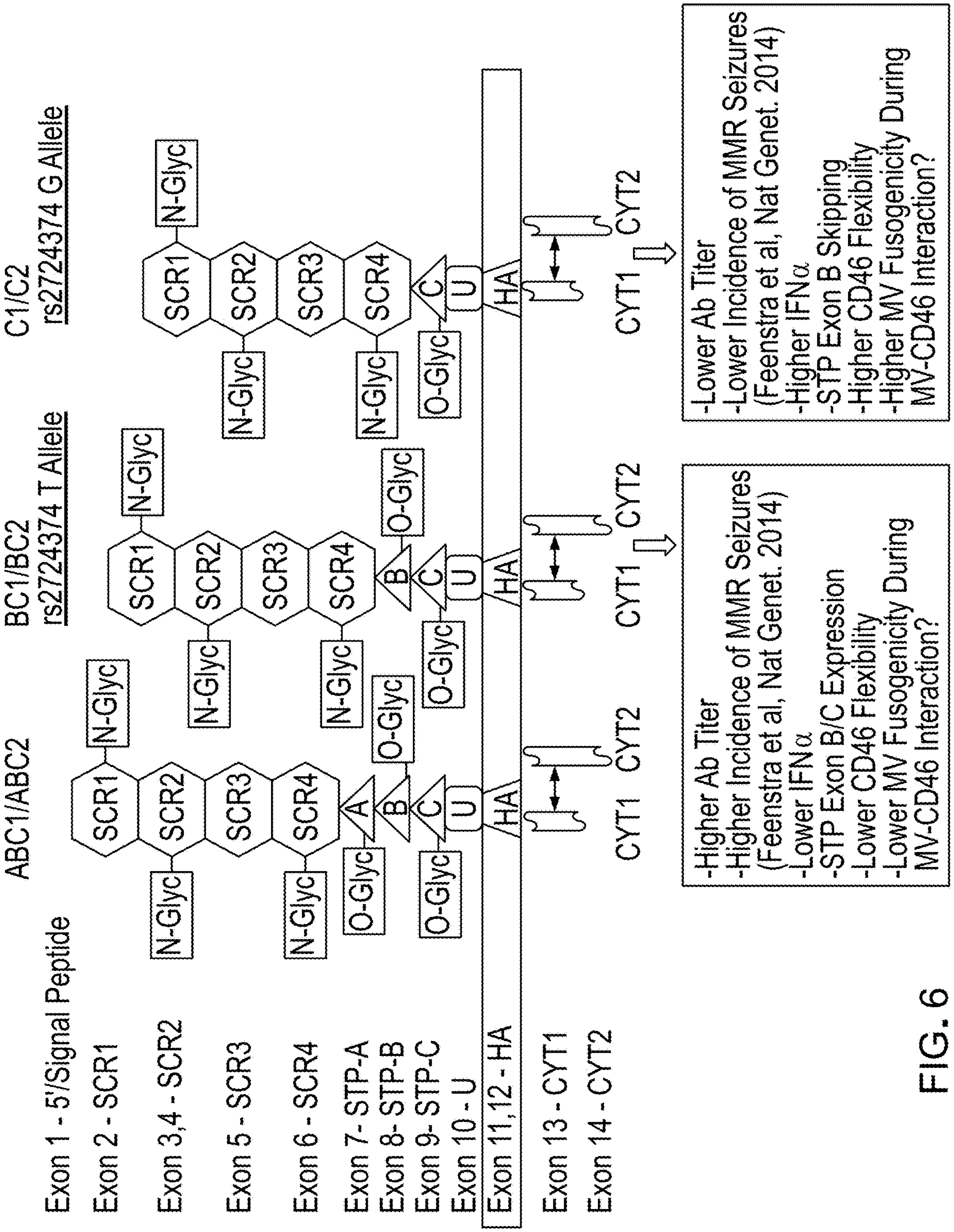
FIG. 6. Structure of CD46. The extracellular portion of CD46 consists of four N-glycosylated conserved short consensus repeats SCR1-4 (SCR1 and SCR2 containing binding sites for MV); a STP region that is O-glycosylated (encoded by exons 7, 8 and 9, designated as A, B and C); and a region of unknown function (U), followed by a hydrophobic transmembrane segment (H), basic amino acid anchor (A), and a cytoplasmic tail (CYT1 of 16 amino acids if exon 13 is present, or CYT2 of 23 amino acids if exon 13 is alternatively spliced). Of the 14 known CD46 isoforms resulting from alternative splicing, four are commonly found in most human tissues and are designated based on the present STP exon/exons and the cytoplasmic tail: BC1 and BC2 (with B and C exons/domains in the STP and with either CYT1 or CYT2), and C1 and C2 (with C exon/domain in the STP and with either CYT1 or CYT2). The effect of CD46 rs2724374 on CD46 isoform prevalence (exon B presence or skipping), interaction between CD46 and MV, and immune response following measles vaccination is also summarized.
Figure 7A:
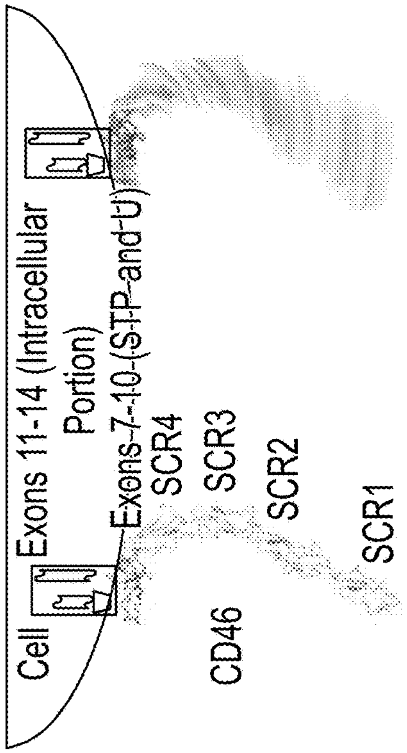
FIGS. 7A-7D. Flexibility of CD46 isoforms and impact on MV-CD46 interactions and MV fusion. (A) CD46 is a cell surface receptor affected by isoform differences. Due in part to its elongated structure, the extracellular domains will naturally exhibit flexibility within the physiologic environment (represented as rotational blurring of the reference isoform ABC1/ABC2). SCR domain residues are colored in yellow. The modeled segment of CD46 includes the extracellular domains and is shown in cartoon representation. (B) Molecular modeling of the extracellular portion of BC1 (BC2) and C1 (C2) isoforms (the four most common isoforms) through SCR4, followed by generation of mechanics-based models (ANM), indicates a difference in the intrinsic flexibility between the isoforms (see FIG. 8 for details). The amino acids encoded by exons 8-10 are indicated by different colors. Representative motion from the ANM models for the BC1 and C1 isoforms are shown by showing multiple conformational states superimposed. (C) CD46 on the cell surface interacts with MV-H on the virion surface. Two CD46 molecules interacting with a MV-H dimer are depicted. Using ANM, the intrinsic flexibility of the MV-H dimer was quantified. The dominant motion is an anti-correlated twisting or ratcheting of the monomers with respect to one another. Projection the effect of this motion onto the bound CD46 molecules is represented by black arrows on each residue. As the C-terminus of CD46 is anchored in the cell membrane, activation of this motion would require flexibility of the CD46 molecule—flexibility that may differ by isoform (panel B). Presented is a second view of the motion rotated 90°, omitting the cartoon representation for clarity—only the motion-vectors are shown to emphasize the twisting of the MV-H dimer and its effect on CD46. (D) Proposed molecular mechanism: MV-H and the fusion protein MV-F are normally associated with one another on the virus surface. Proteins are represented by smoothed molecular surfaces. The encounter complex between CD46 and MV-H leads to MV-F disassociation. The disassociation is influenced by the MV-H conformational change and motion in the context of the CD46-H dimer complex. The free MV-F undergoes a substantial conformational change, the molecular details of which are not fully resolved, leading to bridging between the virus and target cell. The degree of flexibility exhibited by CD46 may influence (a) the ease with which the complex may undergo conformational changes (motion in the context of MV-H-CD46 complex) leading to MV-F triggering and fusion, and (b) the rate of encounter complex formation with MV-H.
Figure 7B:
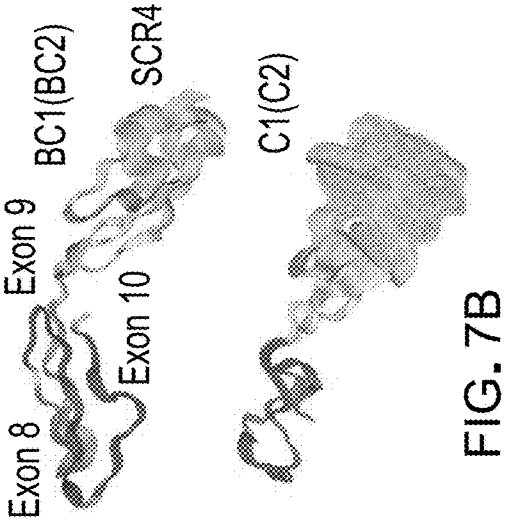
Figure 7C:
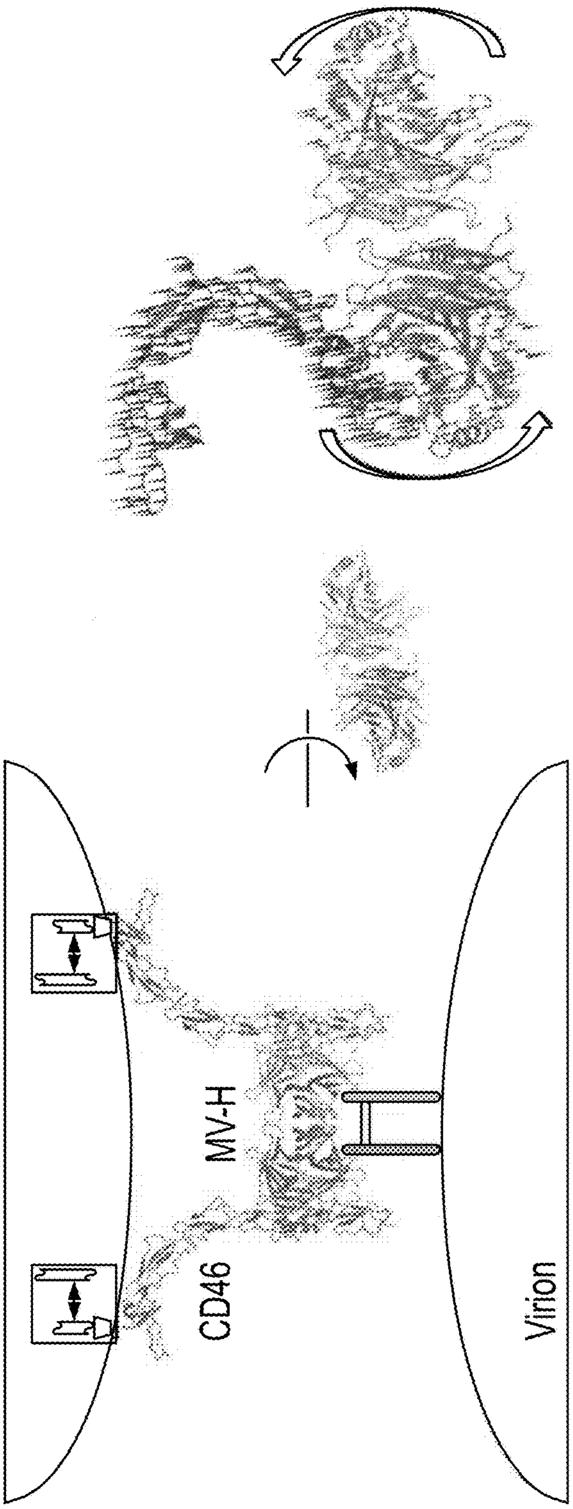
Figure 7D:
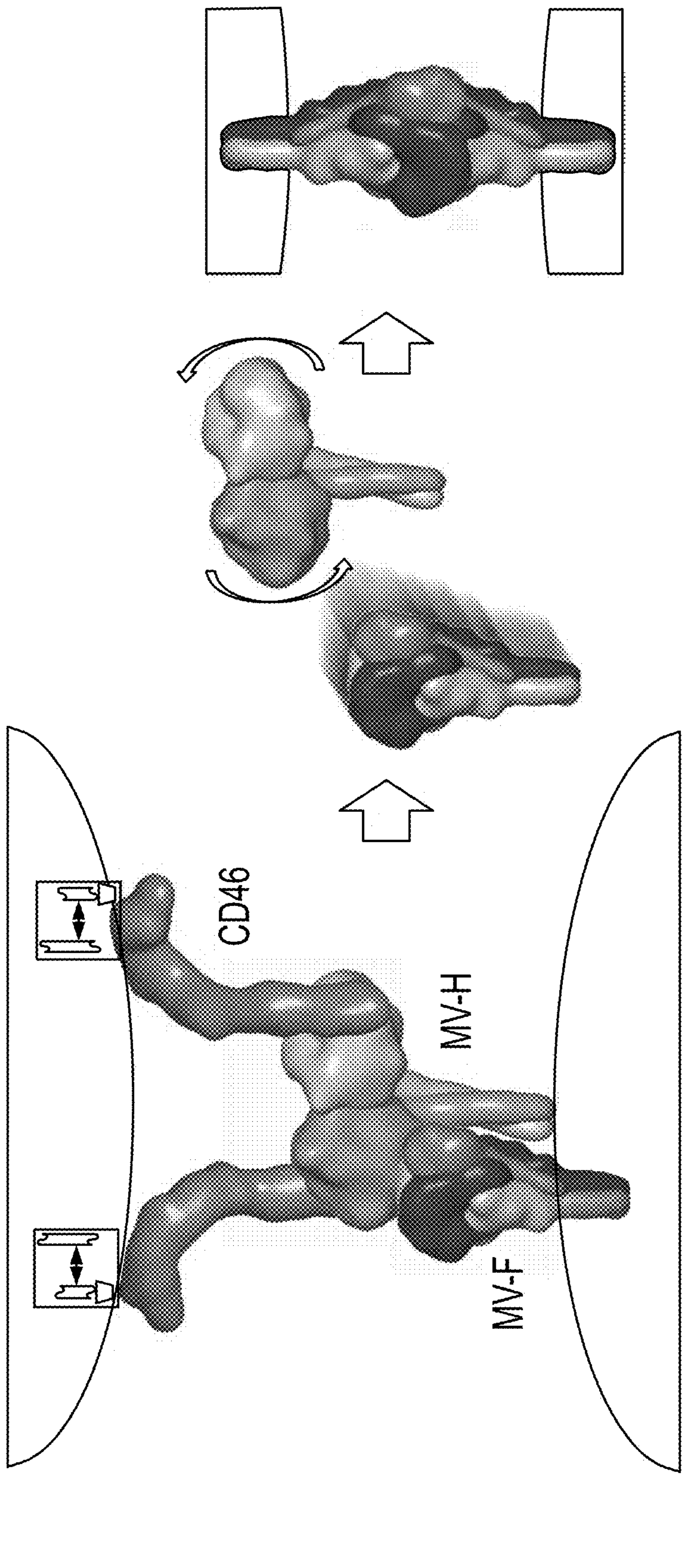
Figure 8A:
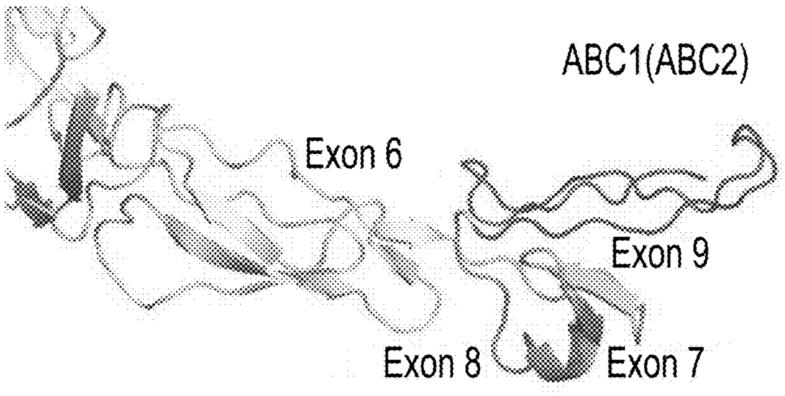
FIGS. 8A-8F. CD46 isoforms exhibit different flexibilities, specifically about the hinge between the SCR4 and STP domains. (A) Molecular structure of the full length CD46, zoomed in to emphasize the differentially spliced exons. (B) Using the first 3 modes of an ANM model, the mobility of each residue was computed. There is increased mobility for the C1 isoform. (inset) The normal mode frequencies are plotted on a log-log scale and indicate a dramatically lower collectivity for the C1 isoform. (C) Commute times are computed for each structure and show a decrease in C1 relative to BC1. (inset) Example matrix of commute times from the BC1 isoform with the N-terminus at the top left and C-terminus bottom right. (D and E) Representative Cα atoms were chosen to define the hinge angle between the exon 6 subdomain, and the subdomain was comprised of the isoform-specific sequences. Panel D for BC1, relatively low mobility about this hinge region is observed (ANM mode 2), while greater flexibility is observed in C1 (ANM mode 2) in E. Representative structures were shown from the ANM modes, deformed to 2 Å RMSD in both directions and superimposed about the sequences encoded by the variable exons. (F) Across the first 5 low-frequency ANM modes, the change in this angle observed when deforming each structure to 2 Å RMSD in each direction was indicated.
Figure 8B:
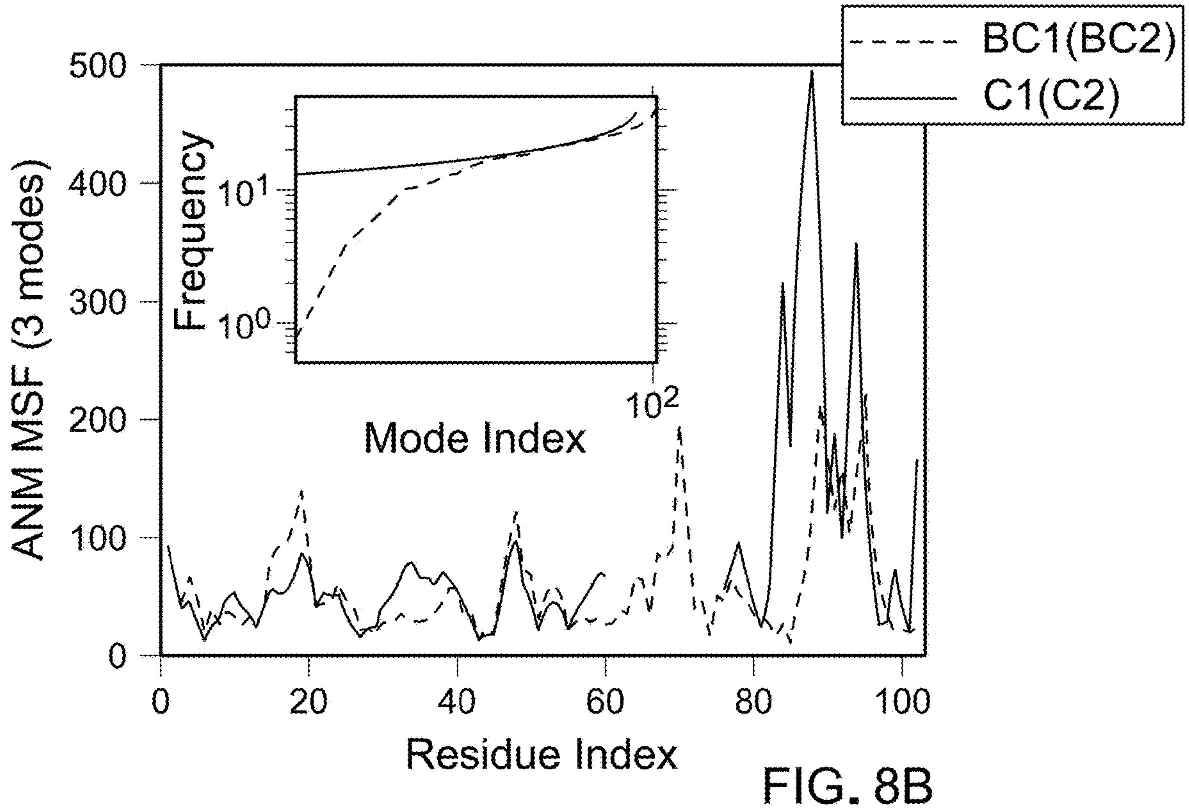
Figure 8C:
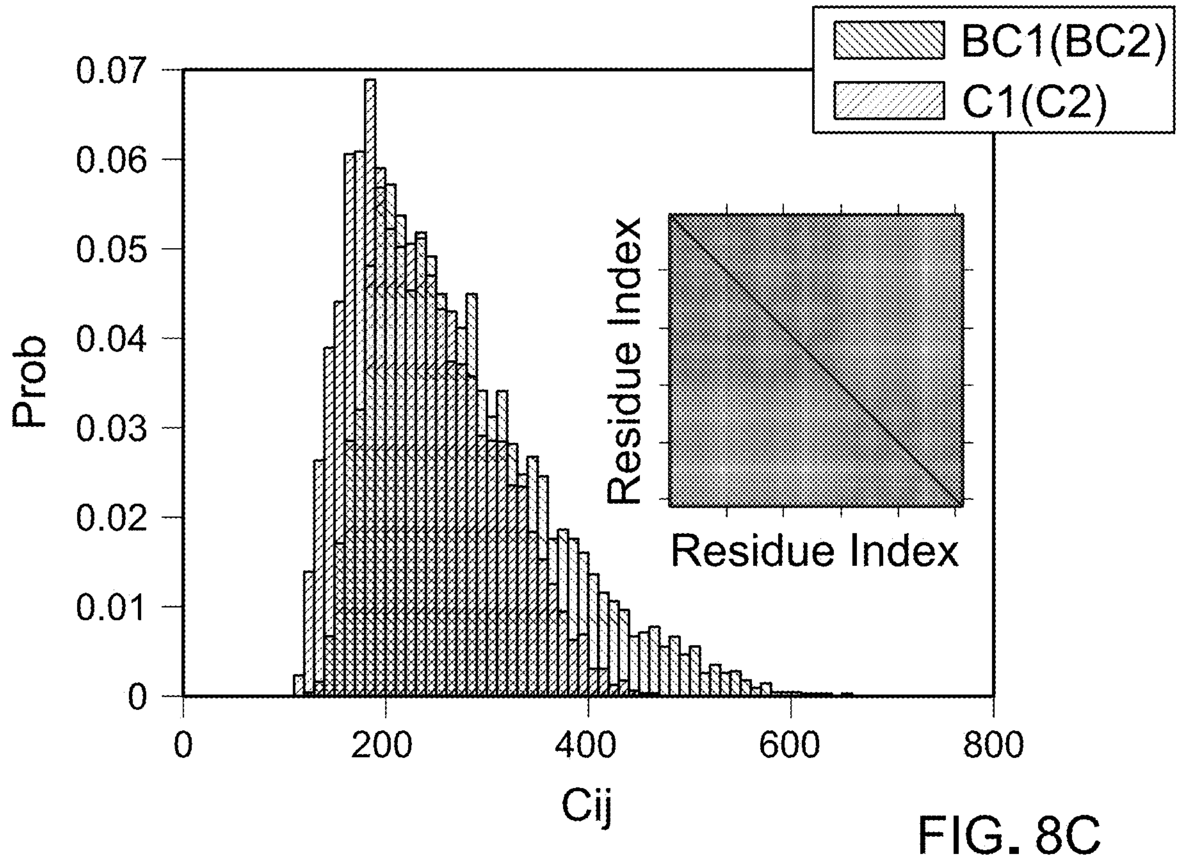
Figure 8D:
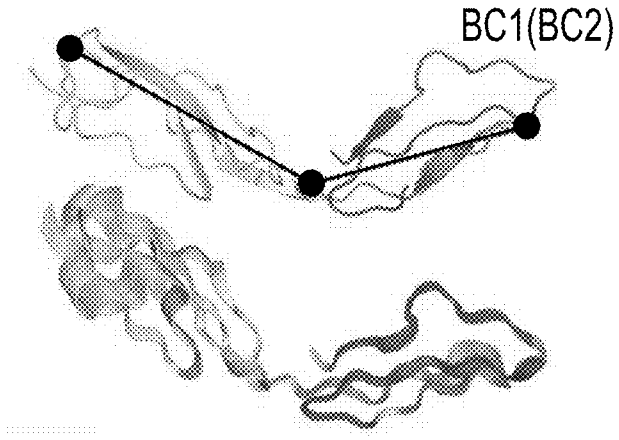
Figure 8E:
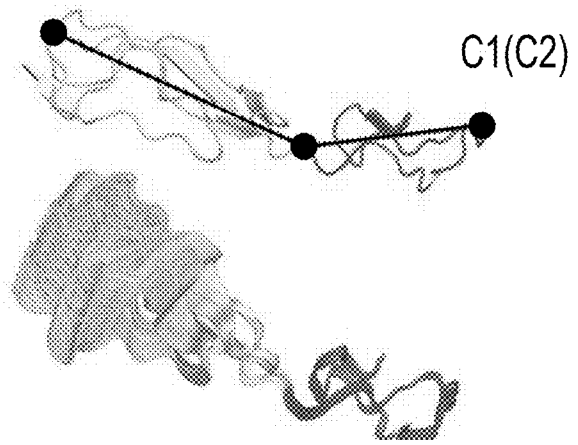
Figure 8F:
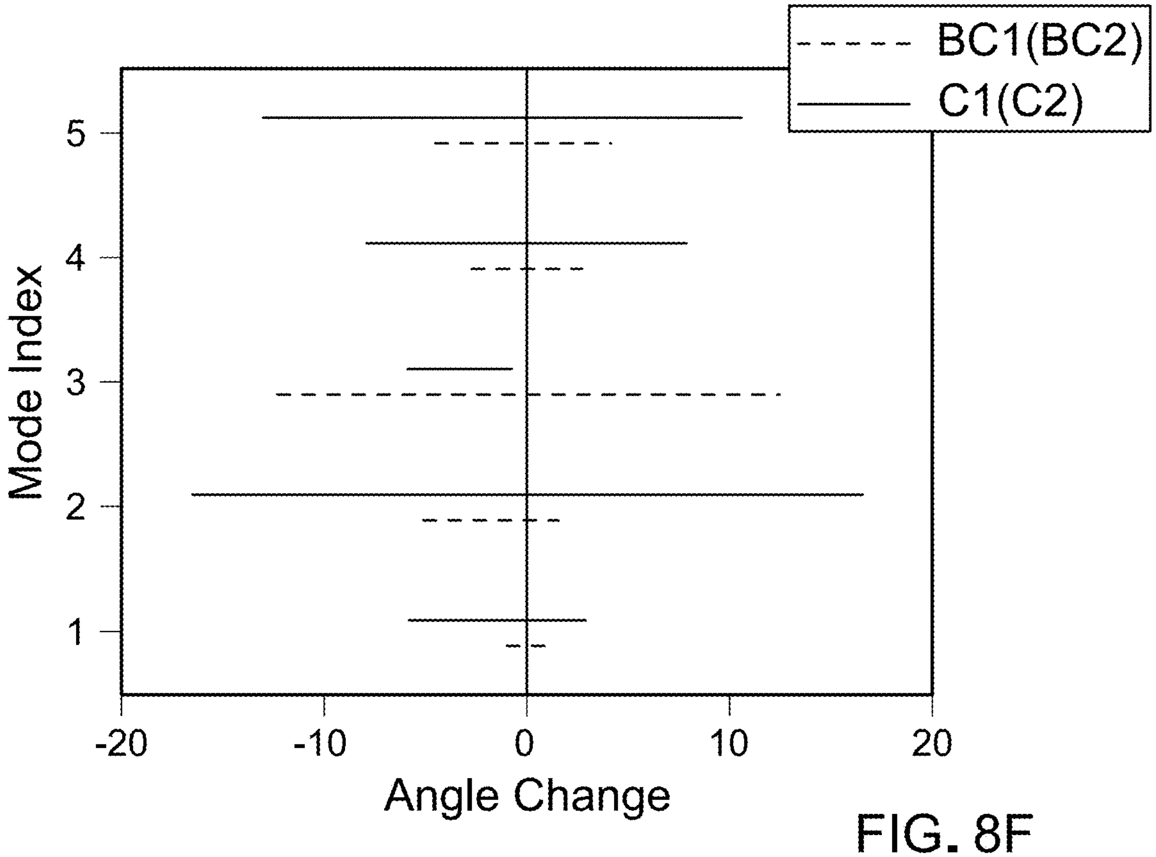

Structural models of the predominant CD46 isoforms (extracellular portion) were generated: isoforms with the STP exons B and C (i.e., BC1 and BC2) and those skipping exon B (i.e., C1 and C2) (FIGS. 6, 7, and 8). The longest isoform, ABC1, generates a high-quality homology model (FIG. 8). Interestingly, the protein sequences encoded by exons A (exon 7) and B (exon 8) have their N- and C-terminal ends close to each other. The amino acids encoded by exon A (exon 7) make a short beta strand within the STP domain. Deletion of these residues by exon skipping removes this strand from the beta-sheet, but the architecture of the domain is not significantly altered. Exon B (8) encodes amino acids making up two additional strands. In the isoforms C1 and C2, only two strands encoded by exons 9 and 10 remain. Computing the dynamics of each isoform's atomic model, the smaller STP domain isoforms exhibited greater flexibility and less collective motion (i.e., in the C1/C2 isoforms when compared to BC1/BC2 of the common isoforms). Monitoring the domain-domain angles about the SCR4-STP hinge as each structure is deformed about its low-frequency normal modes, the shorter isoform/isoforms exhibited a greater range of flexibility (FIG. 8). As illustrated in FIG. 7, based on data from the molecular models, the differential isoform flexibility may influence the rate of formation of the CD46-MV-hemagglutinin (H) encounter complex, and/or influence the propensity for MV-H to undergo the conformational change necessary to trigger MV fusion protein.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for providing a human with a measles virus vaccination, wherein said method comprises:

(a) detecting the presence of the major allele T of CD46 rs2724374, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, or the minor allele C of CD46 rs11806810 in a sample obtained from said human, and (b) administering a measles virus vaccine to said human.

2. The method of claim 1, wherein said method comprise detecting the presence of the major allele T of CD46 rs2724374, the major allele A of CD46 rs2724384, the major allele A of IFI44L rs273259, the major allele T of IFI44L rs1333973, the major allele C of CD46 rs4844619, the major allele C of CD46 rs2466572, the major allele T of CD46 rs2724360, the major allele G of CD46 rs6657476, the major allele A of CD46 rs4844390, the major allele A of IFI44L rs4650590, the major allele G of IFI44L rs6693207, the major allele A of IFI44L rs273255, the major allele G of IFI44L rs273261, the major allele A of IFI44L rs273256, the major allele A of IFI44L rs273244, the major allele T of LOC101929385 rs11118612, the major allele C of LOC101929385 rs4844392, the major allele A of LOC101929385 rs66532523, the major allele G of LOC101929385 rs4844620, the major allele G of intergenic rs2761437, the major allele T of intergenic rs2796265, the major allele G of intergenic rs2761434, the major allele T of intergenic rs56075814, the major allele T of intergenic rs6669384, the major allele T of intergenic rs55935450, the major allele C of intergenic rs11118668, the major allele T of intergenic rs1318653, the major allele T of intergenic rs61821293, the major allele G of intergenic rs273238, the major allele A of intergenic rs12026737, and the minor allele C of CD46 rs11806810 in said sample.

3. The method of claim 1, wherein said measles virus vaccine is a measles, mumps, and rubella vaccine.

4. A method for providing a human with a measles virus vaccination, wherein said method comprises:

(a) detecting the presence of the minor allele G of CD46 rs2724374, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, or the major allele G of CD46 rs11806810 in a sample obtained from said human, and (b) administering an enhanced measles virus vaccine to said human or administering a measles virus vaccine at least three times to said human.

5. The method of claim 4, wherein said method comprise detecting the presence of the minor allele G of CD46 rs2724374, the minor allele G of CD46 rs2724384, the minor allele G of IFI44L rs273259, the minor allele A of IFI44L rs1333973, the minor allele T of CD46 rs4844619, the minor allele A of CD46 rs2466572, the minor allele C of CD46 rs2724360, the minor allele T of CD46 rs6657476, the minor allele G of CD46 rs4844390, the minor allele G of IFI44L rs4650590, the minor allele A of IFI44L rs6693207, the minor allele T of IFI44L rs273255, the minor allele A of IFI44L rs273261, the minor allele C of IFI44L rs273256, the minor allele T of IFI44L rs273244, the minor allele A of LOC101929385 rs11118612, the minor allele G of LOC101929385 rs4844392, the minor allele C of LOC101929385 rs66532523, the minor allele A of LOC101929385 rs4844620, the minor allele A of intergenic rs2761437, the minor allele C of intergenic rs2796265, the minor allele A of intergenic rs2761434, the minor allele C of intergenic rs56075814, the minor allele C of intergenic rs6669384, the minor allele A of intergenic rs55935450, the minor allele T of intergenic rs11118668, the minor allele C of intergenic rs1318653, the minor allele G of intergenic rs61821293, the minor allele A of intergenic rs273238, the minor allele C of intergenic rs12026737, and the major allele G of CD46 rs11806810 in said sample.

6. The method of claim 4, wherein said method comprises administering said measles virus vaccine, and wherein said measles virus vaccine is a measles, mumps, and rubella vaccine.

* * * * *

SEQUENCE LISTING

```
<160> NUMBER OF SEQ ID NOS: 2

<210> SEQ ID NO 1
<211> LENGTH: 28
<212> TYPE: DNA
<213> ORGANISM: Homo sapiens

<400> SEQUENCE: 1

gtggtcaaat gtcgatttcc agtagtcg                                    28


<210> SEQ ID NO 2
<211> LENGTH: 31
<212> TYPE: DNA
<213> ORGANISM: Homo sapiens

<400> SEQUENCE: 2

caagccacat tgcaatatta gctaagccac a                                31
```